United States Patent
Asundi et al.

(10) Patent No.: US 10,889,651 B2
(45) Date of Patent: Jan. 12, 2021

(54) ANTI-LY6E ANTIBODIES AND METHODS OF USE

(71) Applicant: Genentech, Inc., South San Francisco, CA (US)

(72) Inventors: Jyoti Asundi, Foster City, CA (US); Ron Firestein, Burlingame, CA (US); Paul Polakis, Mill Valley, CA (US); Chie Sakanaka, Tokyo (JP); Peter Chang, Greenbrae, CA (US); Rayna Takaki Venook, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 117 days.

(21) Appl. No.: 16/050,936

(22) Filed: Jul. 31, 2018

(65) Prior Publication Data

US 2019/0085089 A1    Mar. 21, 2019

Related U.S. Application Data

(62) Division of application No. 15/018,710, filed on Feb. 8, 2016, now Pat. No. 10,066,022, which is a division of application No. 14/518,294, filed on Oct. 20, 2014, now Pat. No. 9,290,578.

(60) Provisional application No. 61/893,553, filed on Oct. 21, 2013.

(51) Int. Cl.
| | | |
|---|---|---|
| C07K 16/30 | (2006.01) | |
| G01N 33/574 | (2006.01) | |
| A61K 47/68 | (2017.01) | |
| A61K 51/10 | (2006.01) | |
| A61K 39/00 | (2006.01) | |

(52) U.S. Cl.
CPC .......... *C07K 16/30* (2013.01); *A61K 47/6803* (2017.08); *A61K 47/6851* (2017.08); *A61K 51/1045* (2013.01); *G01N 33/574* (2013.01); *G01N 33/57415* (2013.01); *G01N 33/57419* (2013.01); *G01N 33/57423* (2013.01); *G01N 33/57438* (2013.01); *G01N 33/57446* (2013.01); *G01N 33/57449* (2013.01); *G01N 33/57492* (2013.01); *A61K 2039/505* (2013.01); *C07K 2317/34* (2013.01); *G01N 2333/705* (2013.01)

(58) Field of Classification Search
CPC ................ C07K 16/30; C07K 2317/34; A61K 47/6851; A61K 47/6803; G01N 33/574
USPC ............................................. 424/1.49, 133.1
See application file for complete search history.

(56) References Cited

U.S. PATENT DOCUMENTS

| | | | |
|---|---|---|---|
| 5,773,223 A | 6/1998 | Shyamala et al. | |
| 6,214,345 B1 | 4/2001 | Firestone et al. | |
| 7,303,749 B1 | 4/2007 | Chari et al. | |
| 7,387,772 B1 | 6/2008 | Hansen et al. | |
| 7,498,298 B2 | 3/2009 | Doronina et al. | |
| 7,521,541 B2 | 4/2009 | Eigenbrot et al. | |
| 7,601,354 B2 | 10/2009 | Chari et al. | |
| 7,659,241 B2 | 2/2010 | Senter et al. | |
| 7,745,394 B2 | 6/2010 | Doronina et al. | |
| 7,829,531 B2 | 11/2010 | Senter et al. | |
| 7,851,437 B2 | 12/2010 | Senter et al. | |
| 7,855,275 B2 | 12/2010 | Eigenbrot et al. | |
| 7,964,566 B2 | 6/2011 | Doronina et al. | |
| 7,964,567 B2 | 6/2011 | Doronina et al. | |
| 7,994,135 B2 | 8/2011 | Doronina et al. | |
| 8,088,387 B2 | 1/2012 | Steeves et al. | |
| 8,142,784 B2 | 3/2012 | Ebens et al. | |
| 8,198,417 B2 | 6/2012 | Steeves et al. | |
| 8,309,300 B2 | 11/2012 | Junutula et al. | |
| 8,557,780 B2 | 10/2013 | Doronina et al. | |
| 10,066,022 B2 * | 9/2018 | Asundi ............ | G01N 33/57449 |
| 2004/0185040 A1 | 9/2004 | Garcia-Martinez et al. | |
| 2006/0094676 A1 | 5/2006 | Lahav | |
| 2007/0269442 A1 | 11/2007 | Webber | |
| 2008/0075712 A1 | 3/2008 | Hattori | |
| 2009/0130108 A1 | 5/2009 | Reiter | |
| 2012/0148610 A1 | 6/2012 | Doronina et al. | |
| 2012/0225060 A1 | 9/2012 | Lee et al. | |
| 2016/0130358 A1 | 5/2016 | Bhakta et al. | |
| 2016/0199508 A1 | 7/2016 | Sakanaka et al. | |
| 2017/0002086 A1 | 1/2017 | Polakis et al. | |

FOREIGN PATENT DOCUMENTS

| | | |
|---|---|---|
| JP | 2006-515751 A | 6/2006 |
| JP | 2009-530645 A | 8/2009 |
| WO | 2004/016225 | 2/2004 |
| WO | WO 2004/045516 A2 | 6/2004 |
| WO | 2005/068503 | 7/2005 |
| WO | 2005/081711 | 9/2005 |
| WO | 2005/082023 | 9/2005 |
| WO | 2005/117986 | 12/2005 |
| WO | 2006/034488 | 3/2006 |
| WO | 2006/060533 | 6/2006 |
| WO | 2007/064345 | 6/2007 |
| WO | 2007/100385 | 9/2007 |
| WO | WO 2007/109347 A2 | 9/2007 |

(Continued)

OTHER PUBLICATIONS

Asundi et al (Clin Cancer Res. Jul. 15, 2015;21(14):3252-62. doi: 10.1158/1078-0432.CCR-15-0156. Epub Apr. 10, 2015).*
Jubb et al. Methods Mol Biol, 2006; 326:255-264.*
International Search Report for PCT/US13/41848, dated Jan. 10, 2014.
International Search Report for PCT/US14/61342, dated Jan. 29, 2015.
GenBank Accession No. ACV51637.1, Hypothetical Protein Apar_1209 [Atopobium Parvulum DSM 20469] (C8W847_ATOPD_, Jun. 4, 2010.

(Continued)

*Primary Examiner* — Lynn A Bristol
(74) *Attorney, Agent, or Firm* — McNeill Baur PLLC

(57) ABSTRACT

The invention provides anti-Ly6E antibodies, immunoconjugates and methods of using the same.

20 Claims, 17 Drawing Sheets

Specification includes a Sequence Listing.

(56) References Cited

FOREIGN PATENT DOCUMENTS

| WO | 1999/055842 | 11/2009 |
|----|-------------|---------|
| WO | 2010/009124 | 1/2010 |
| WO | 2010/099273 | 9/2010 |
| WO | 2011/051349 | 5/2011 |
| WO | 2011/056983 | 5/2011 |
| WO | 2011/106297 | 9/2011 |
| WO | 2011/156328 | 12/2011 |
| WO | 2012/074757 | 6/2012 |
| WO | 2013/177055 | 11/2013 |

OTHER PUBLICATIONS

GenBank Accession No. CAJ48864.1, Putative Membrane Protein [Bordetella Avium 197N] (Q2L324_BORA1), Nov. 5, 2010.

Baca, M. et al., "Antibody Humanization Using Monovalent Phage Display," Journal of Biological Chemistry, vol. 272, No. 16, 1997, pp. 10678-10684.

Dent, R. et al., "Triple-Negative Breast Cancer: Clinical Features and Patterns of Recurrence," Clinical Cancer Research, 13, 2007, pp. 4429-4434.

Spieker-Polet, et al., "Rabbit Monoclonal Antibodies: Generating a Fusion Partner to Produce Rabbit-Rabbit Hybridomas," Proc. Natl. Acad. Sci. USA, vol. 92, Sep. 1995, pp. 9348-9352.

U.S. Appl. No. 14/119,835, filed Nov. 22, 2013.

Asundi et al., "An Antibody-Drug Conjugate Directed against Lymphocyte Antigen 6 Complex, Locus E (LY6E) Provides Robust Tumor Killing in a Wide Range of Solid Tumor Malignancies," Clin. Cancer Res., 21(14): 3252-3262 (Jul. 15, 2015).

Asundi et al., "Abstract 947: An antibody drug conjugate (ADC) directed to lymphocyte antigen 6 complex, locus E (LY6E) delivers targeted chemotherapy to a wide range of solid tumor malignancies," Proceedings: AACR 106th Annual Meeting 2015, Apr. 18-22, 2015, Philadelphia, PA, Cancer Research, 75(15, Supp.): 947 (2015).

Gou et al. "Establishment of Clonal Colony-Forming Assay for Propagation of Pancreatic Cancer Cells With Stem Cell Properties," Pancreas, 34(4): 429-435 (2007).

Green et al., "Abstract 101: Characterization of the interferon alpha inducible protein LY6E," Cytokine, 63(3, special issue): 267 (2013).

Hughes et al., "Ly6e expression is restricted to syncytiotrophoblast cells of the mouse placenta," Placenta, 34(9): 831-835 (2013).

Extended European Search Report, for European Patent Application No. 14856653.2, dated Apr. 21, 2017 (11 pages).

* cited by examiner

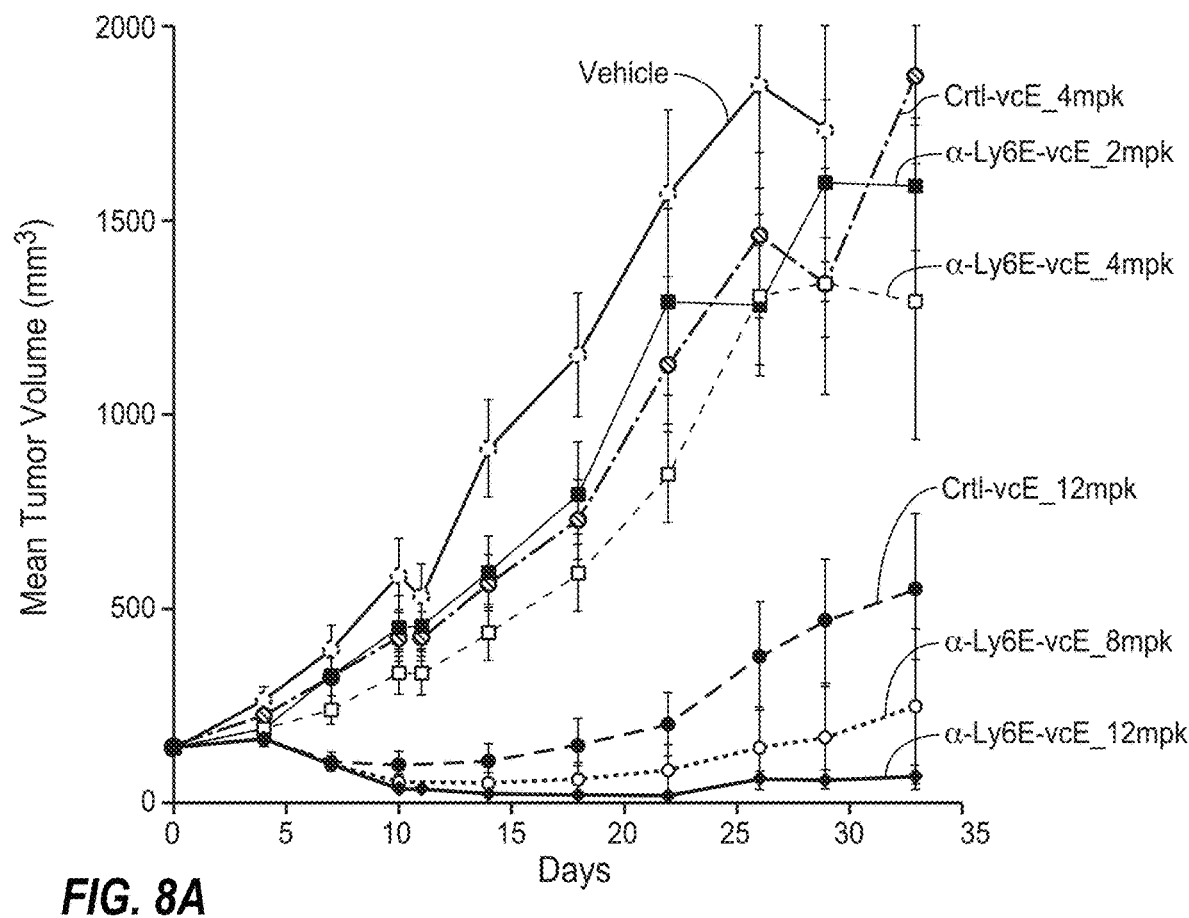
FIG. 8A
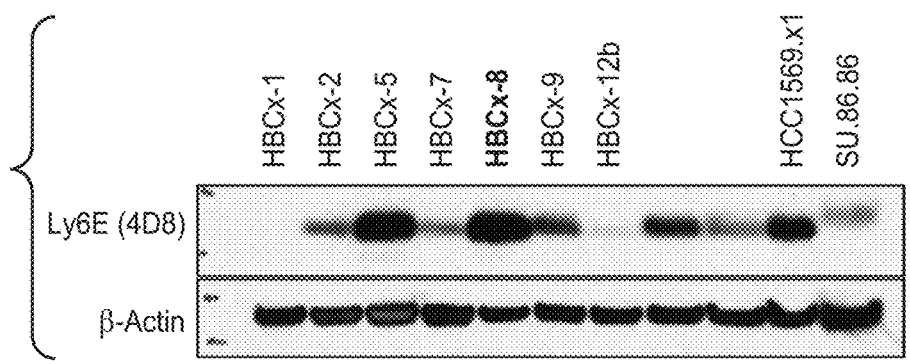
FIG. 8B
FIG. 8C

2+

SEQUENCE LISTING

```
<160> NUMBER OF SEQ ID NOS: 53

<210> SEQ ID NO 1
<211> LENGTH: 131
<212> TYPE: PRT
<213> ORGANISM: Homo sapiens

<400> SEQUENCE: 1

Met Lys Ile Phe Leu Pro Val Leu Leu Ala Ala Leu Leu Gly Val Glu
1               5                   10                  15

Arg Ala Ser Ser Leu Met Cys Phe Ser Cys Leu Asn Gln Lys Ser Asn
            20                  25                  30

Leu Tyr Cys Leu Lys Pro Thr Ile Cys Ser Asp Gln Asp Asn Tyr Cys
        35                  40                  45

Val Thr Val Ser Ala Ser Ala Gly Ile Gly Asn Leu Val Thr Phe Gly
    50                  55                  60

His Ser Leu Ser Lys Thr Cys Ser Pro Ala Cys Pro Ile Pro Glu Gly
65                  70                  75                  80

Val Asn Val Gly Val Ala Ser Met Gly Ile Ser Cys Cys Gln Ser Phe
                85                  90                  95

Leu Cys Asn Phe Ser Ala Ala Asp Gly Gly Leu Arg Ala Ser Val Thr
            100                 105                 110
```

```
Leu Leu Gly Ala Gly Leu Leu Leu Ser Leu Leu Pro Ala Leu Leu Arg
            115                 120                 125

Phe Gly Pro
    130

<210> SEQ ID NO 2
<211> LENGTH: 131
<212> TYPE: PRT
<213> ORGANISM: Macaca fascicularis

<400> SEQUENCE: 2

Met Lys Ile Phe Leu Pro Val Leu Leu Ala Ala Leu Leu Gly Val Glu
1               5                   10                  15

Arg Ala Ser Ser Leu Met Cys Phe Ser Cys Leu Asn Gln Lys Ser Asn
                20                  25                  30

Leu Tyr Cys Leu Lys Pro Thr Ile Cys Ser Asp Gln Asp Asn Tyr Cys
            35                  40                  45

Val Thr Val Ser Thr Ser Ala Gly Ile Gly Asn Leu Val Thr Phe Gly
        50                  55                  60

His Ser Leu Ser Lys Thr Cys Ser Pro Ala Cys Pro Leu Pro Glu Gly
65                  70                  75                  80

Ile Asn Val Gly Val Ala Ser Met Gly Ile Ser Cys Cys Gln Ser Phe
                85                  90                  95

Leu Cys Asn Phe Ser Ala Ala Asp Gly Gly Leu Arg Ala Ser Ala Thr
            100                 105                 110

Leu Leu Gly Ala Gly Leu Leu Leu Ser Leu Leu Pro Ala Leu Leu Arg
        115                 120                 125

Phe Gly Pro
    130

<210> SEQ ID NO 3
<211> LENGTH: 107
<212> TYPE: PRT
<213> ORGANISM: Artificial sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Gly Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Asn Leu His Ser Gly Val Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Tyr Ser Glu Leu Pro Trp
                85                  90                  95

Thr Phe Gly Gln Gly Thr Lys Val Glu Ile Lys
            100                 105

<210> SEQ ID NO 4
<211> LENGTH: 107
<212> TYPE: PRT
<213> ORGANISM: Artificial sequence
<220> FEATURE:
<223> OTHER INFORMATION: Synthetic
```

```
<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Glu Leu Pro Trp
                85                  90                  95

Thr Phe Gly Gly Gly Thr Lys Val Glu Ile Lys
            100                 105

<210> SEQ ID NO 5
<211> LENGTH: 120
<212> TYPE: PRT
<213> ORGANISM: Artificial sequence
<220> FEATURE:
<223> OTHER INFORMATION: Synthetic

<400> SEQUENCE: 5

Glu Val Gln Leu Val Glu Ser Gly Pro Ala Leu Val Lys Pro Thr Gln
1               5                   10                  15

Thr Leu Thr Leu Thr Cys Thr Val Ser Gly Phe Ser Leu Thr Gly Tyr
            20                  25                  30

Ser Val Asn Trp Ile Arg Gln Pro Pro Gly Lys Ala Leu Glu Trp Leu
        35                  40                  45

Gly Met Ile Trp Gly Asp Gly Ser Thr Asp Tyr Asn Ser Ala Leu Lys
50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Arg Asp Tyr Tyr Phe Asn Tyr Ala Ser Trp Phe Ala Tyr Trp Gly Gln
            100                 105                 110

Gly Thr Leu Val Thr Val Ser Ser
        115                 120

<210> SEQ ID NO 6
<211> LENGTH: 120
<212> TYPE: PRT
<213> ORGANISM: Artificial sequence
<220> FEATURE:
<223> OTHER INFORMATION: Synthetic

<400> SEQUENCE: 6

Gln Val Gln Leu Lys Glu Ser Gly Pro Gly Leu Val Ala Pro Ser Gln
1               5                   10                  15

Ser Leu Ser Leu Thr Cys Thr Val Ser Gly Phe Ser Leu Thr Gly Tyr
            20                  25                  30

Ser Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
50                  55                  60
```

Ser Arg Leu Thr Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
            85                  90                  95

Arg Asp Tyr Tyr Phe Asn Tyr Ala Ser Trp Phe Ala Trp Gly Pro
        100                 105                 110

Gly Thr Leu Val Thr Val Ser Ala
        115                 120

<210> SEQ ID NO 7
<211> LENGTH: 11
<212> TYPE: PRT
<213> ORGANISM: Artificial sequence
<220> FEATURE:
<223> OTHER INFORMATION: Synthetic

<400> SEQUENCE: 7

Ser Ala Ser Gln Gly Ile Ser Asn Tyr Leu Asn
1               5                   10

<210> SEQ ID NO 8
<211> LENGTH: 7
<212> TYPE: PRT
<213> ORGANISM: Artificial sequence
<220> FEATURE:
<223> OTHER INFORMATION: Synthetic

<400> SEQUENCE: 8

Tyr Thr Ser Asn Leu His Ser
1               5

<210> SEQ ID NO 9
<211> LENGTH: 9
<212> TYPE: PRT
<213> ORGANISM: Artificial sequence
<220> FEATURE:
<223> OTHER INFORMATION: Synthetic

<400> SEQUENCE: 9

Gln Gln Tyr Ser Glu Leu Pro Trp Thr
1               5

<210> SEQ ID NO 10
<211> LENGTH: 10
<212> TYPE: PRT
<213> ORGANISM: Artificial sequence
<220> FEATURE:
<223> OTHER INFORMATION: Synthetic

<400> SEQUENCE: 10

Gly Phe Ser Leu Thr Gly Tyr Ser Val Asn
1               5                   10

<210> SEQ ID NO 11
<211> LENGTH: 16
<212> TYPE: PRT
<213> ORGANISM: Artificial sequence
<220> FEATURE:
<223> OTHER INFORMATION: Synthetic

<400> SEQUENCE: 11

Met Ile Trp Gly Asp Gly Ser Thr Asp Tyr Asn Ser Ala Leu Lys Ser
1               5                   10                  15

<210> SEQ ID NO 12
<211> LENGTH: 12
<212> TYPE: PRT
<213> ORGANISM: Artificial sequence
<220> FEATURE:
<223> OTHER INFORMATION: Synthetic

<400> SEQUENCE: 12

Asp Tyr Tyr Val Asn Tyr Ala Ser Trp Phe Ala Tyr
1               5                   10

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19
<211> LENGTH: 23
<212> TYPE: PRT
<213> ORGANISM: Artificial sequence
<220> FEATURE:
<223> OTHER INFORMATION: Synthetic

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 20
<211> LENGTH: 15
<212> TYPE: PRT
<213> ORGANISM: Artificial sequence
<220> FEATURE:
<223> OTHER INFORMATION: Synthetic

<400> SEQUENCE: 20

Trp Tyr Gln Gln Lys Pro Gly Lys Thr Val Lys Leu Leu Ile Tyr
1               5                   10                  15

<210> SEQ ID NO 21
<211> LENGTH: 32
<212> TYPE: PRT
<213> ORGANISM: Artificial sequence
<220> FEATURE:
<223> OTHER INFORMATION: Synthetic

<400> SEQUENCE: 21

Gly Val Pro Ser Arg Phe Ser Gly Ser Gly Ser Gly Thr Asp Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 22
<211> LENGTH: 10
<212> TYPE: PRT
<213> ORGANISM: Artificial sequence
<220> FEATURE:
<223> OTHER INFORMATION: Synthetic

<400> SEQUENCE: 22

Phe Gly Gln Gly Thr Lys Val Glu Ile Lys
1               5                   10

<210> SEQ ID NO 23
<211> LENGTH: 25
<212> TYPE: PRT
<213> ORGANISM: Artificial sequence
<220> FEATURE:
<223> OTHER INFORMATION: Synthetic

<400> SEQUENCE: 23

Glu Val Gln Leu Val Glu Ser Gly Pro Ala Leu Val Lys Pro Thr Gln
1               5                   10                  15

Thr Leu Thr Leu Thr Cys Thr Val Ser
            20                  25

<210> SEQ ID NO 24
<211> LENGTH: 14
<212> TYPE: PRT
<213> ORGANISM: Artificial sequence
<220> FEATURE:
<223> OTHER INFORMATION: Synthetic

<400> SEQUENCE: 24

Trp Ile Arg Gln Pro Pro Gly Lys Ala Leu Glu Trp Leu Gly
1               5                   10

<210> SEQ ID NO 25
<211> LENGTH: 32
<212> TYPE: PRT
<213> ORGANISM: Artificial sequence
<220> FEATURE:
<223> OTHER INFORMATION: Synthetic

<400> SEQUENCE: 25

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

```
<210> SEQ ID NO 26
<211> LENGTH: 11
<212> TYPE: PRT
<213> ORGANISM: Artificial sequence
<220> FEATURE:
<223> OTHER INFORMATION: Synthetic

<400> SEQUENCE: 26

Trp Gly Gln Gly Thr Leu Val Thr Val Ser Ser
1               5                   10

<210> SEQ ID NO 27
<211> LENGTH: 110
<212> TYPE: PRT
<213> ORGANISM: Lepus curpaeums

<400> SEQUENCE: 27

Asp Pro Val Val Thr Gln Thr Pro Ser Ser Ala Ser Ala Ala Val Gly
1               5                   10                  15

Gly Thr Val Ser Ile Ser Cys Gln Ser Ser Gln Ser Val Tyr Asn Asn
                20                  25                  30

Asn Tyr Leu Gly Trp Tyr Gln Gln Lys Pro Gly Gln Pro Pro Lys Leu
            35                  40                  45

Leu Ile Tyr Asp Ala Ser Lys Leu Ala Ser Gly Val Pro Ser Arg Phe
    50                  55                  60

Lys Ala Ser Gly Ser Gly Thr Gln Phe Ala Leu Thr Ile Ser Asp Leu
65                  70                  75                  80

Glu Cys Asp Asp Ala Ala Thr Tyr Tyr Cys Val Gly Gly Tyr Pro Gly
                85                  90                  95

Ser Leu Asn Val Phe Gly Gly Gly Thr Glu Val Val Val Lys
            100                 105                 110

<210> SEQ ID NO 28
<211> LENGTH: 113
<212> TYPE: PRT
<213> ORGANISM: Lepus curpaeums

<400> SEQUENCE: 28

Gln Ser Val Glu Glu Ser Gly Gly Arg Leu Val Thr Pro Gly Thr Pro
1               5                   10                  15

Leu Thr Leu Thr Cys Ala Thr Ser Gly Phe Ser Leu Ser Ile Tyr Asp
                20                  25                  30

Met Thr Trp Val Arg Gln Ala Pro Gly Lys Gly Leu Glu Trp Ile Gly
            35                  40                  45

Val Ile Tyr Thr Ser Gly Gly Ala Tyr Tyr Ala Asn Trp Ala Lys Gly
    50                  55                  60

Arg Phe Thr Ile Ser Arg Thr Ser Thr Val Asp Leu Arg Met Thr
65                  70                  75                  80

Ser Pro Thr Thr Glu Asp Thr Ala Thr Tyr Phe Cys Val Arg Asn Trp
                85                  90                  95

Ala His Gly Ser Asp Leu Trp Gly Gln Gly Thr Leu Val Thr Val Ser
            100                 105                 110

Ser

<210> SEQ ID NO 29
<211> LENGTH: 13
<212> TYPE: PRT
<213> ORGANISM: Artificial sequence
<220> FEATURE:
<223> OTHER INFORMATION: Synthetic
```

```
<400> SEQUENCE: 29

Gln Ser Ser Gln Ser Val Tyr Asn Asn Asn Tyr Leu Gly
1               5                   10

<210> SEQ ID NO 30
<211> LENGTH: 7
<212> TYPE: PRT
<213> ORGANISM: Artificial sequence
<220> FEATURE:
<223> OTHER INFORMATION: Synthetic

<400> SEQUENCE: 30

Asp Ala Ser Lys Leu Ala Ser
1               5

<210> SEQ ID NO 31
<211> LENGTH: 10
<212> TYPE: PRT
<213> ORGANISM: Artificial sequence
<220> FEATURE:
<223> OTHER INFORMATION: Synthetic

<400> SEQUENCE: 31

Val Gly Gly Tyr Pro Gly Ser Leu Asn Val
1               5                   10

<210> SEQ ID NO 32
<211> LENGTH: 5
<212> TYPE: PRT
<213> ORGANISM: Artificial sequence
<220> FEATURE:
<223> OTHER INFORMATION: Synthetic

<400> SEQUENCE: 32

Ile Tyr Asp Met Thr
1               5

<210> SEQ ID NO 33
<211> LENGTH: 14
<212> TYPE: PRT
<213> ORGANISM: Artificial sequence
<220> FEATURE:
<223> OTHER INFORMATION: Synthetic

<400> SEQUENCE: 33

Val Ile Tyr Thr Ser Gly Gly Ala Tyr Tyr Ala Asn Trp Ala
1               5                   10

<210> SEQ ID NO 34
<211> LENGTH: 8
<212> TYPE: PRT
<213> ORGANISM: Artificial sequence
<220> FEATURE:
<223> OTHER INFORMATION: Synthetic

<400> SEQUENCE: 34

Asn Trp Ala His Gly Ser Asp Leu
1               5

<210> SEQ ID NO 35
<211> LENGTH: 131
<212> TYPE: PRT
<213> ORGANISM: Macaca mulatta

<400> SEQUENCE: 35
```

```
Met Lys Ile Phe Leu Pro Val Leu Leu Ala Leu Leu Gly Val Glu
1               5                   10                  15

Arg Ala Ser Ser Leu Met Cys Phe Ser Cys Leu Asn Gln Lys Ser Asn
                20                  25                  30

Leu Tyr Cys Leu Lys Pro Thr Ile Cys Ser Asp Gln Asp Asn Tyr Cys
            35                  40                  45

Val Thr Val Ser Thr Ser Ala Gly Ile Gly Asn Leu Val Thr Phe Gly
    50                  55                  60

His Ser Leu Ser Lys Thr Cys Ser Pro Ala Cys Pro Leu Pro Glu Gly
65                  70                  75                  80

Ile Asn Val Gly Val Ala Ser Met Gly Ile Ser Cys Cys Gln Ser Phe
                85                  90                  95

Leu Cys Asn Phe Ser Ala Ala Asp Gly Gly Leu Arg Ala Ser Ala Thr
            100                 105                 110

Leu Leu Gly Ala Gly Leu Leu Leu Ser Leu Leu Pro Ala Leu Leu Arg
        115                 120                 125

Phe Gly Pro
        130

<210> SEQ ID NO 36
<211> LENGTH: 136
<212> TYPE: PRT
<213> ORGANISM: Mus musculus

<400> SEQUENCE: 36

Met Ser Ala Thr Ser Asn Met Arg Val Phe Leu Pro Val Leu Leu Ala
1               5                   10                  15

Ala Leu Leu Gly Met Glu Gln Val His Ser Leu Met Cys Phe Ser Cys
                20                  25                  30

Thr Asp Gln Lys Asn Asn Ile Asn Cys Leu Trp Pro Val Ser Cys Gln
            35                  40                  45

Glu Lys Asp His Tyr Cys Ile Thr Leu Ser Ala Ala Gly Phe Gly
    50                  55                  60

Asn Val Asn Leu Gly Tyr Thr Leu Asn Lys Gly Cys Ser Pro Ile Cys
65                  70                  75                  80

Pro Ser Glu Asn Val Asn Leu Asn Leu Gly Val Ala Ser Val Asn Ser
                85                  90                  95

Tyr Cys Cys Gln Ser Ser Phe Cys Asn Phe Ser Ala Ala Gly Leu Gly
            100                 105                 110

Leu Arg Ala Ser Ile Pro Leu Leu Gly Leu Gly Leu Leu Leu Ser Leu
        115                 120                 125

Leu Ala Leu Leu Gln Leu Ser Pro
130                 135

<210> SEQ ID NO 37
<211> LENGTH: 136
<212> TYPE: PRT
<213> ORGANISM: Rat rattus

<400> SEQUENCE: 37

Met Ser Ala Ala Ser Ser Met Arg Val Phe Leu Pro Val Leu Leu Ala
1               5                   10                  15

Ala Leu Leu Gly Val Glu Gln Val His Ser Leu Met Cys Phe Ser Cys
                20                  25                  30

Thr Asp Gln Lys Asn Asn Ile Asn Cys Leu Trp Pro Val Ser Cys Ser
            35                  40                  45
```

Ser Thr Asp Asn Tyr Cys Ile Thr Leu Ser Ala Ala Ala Gly Phe Gly
        50                  55                  60

Asn Val Asn Leu Gly Tyr Thr Leu Asn Lys Gly Cys Ser Pro Thr Cys
 65                  70                  75                  80

Pro Arg Glu Asn Ile Asn Ile Asn Leu Gly Val Ala Ser Val Asn Ser
                 85                  90                  95

Tyr Cys Cys Gln Ser Ser Phe Cys Asn Phe Ser Thr Ala Gly Leu Gly
                100                 105                 110

Leu Arg Ala Ser Ile Pro Leu Leu Gly Leu Gly Leu Leu Leu Ser Leu
                115                 120                 125

Leu Ala Val Leu Arg Leu Ser Pro
130                 135

<210> SEQ ID NO 38
<211> LENGTH: 111
<212> TYPE: PRT
<213> ORGANISM: Homo sapiens

<400> SEQUENCE: 38

Leu Met Cys Phe Ser Cys Leu Asn Gln Lys Ser Asn Leu Tyr Cys Leu
 1               5                  10                  15

Lys Pro Thr Ile Cys Ser Asp Gln Asp Asn Tyr Cys Val Thr Val Ser
                 20                  25                  30

Ala Ser Ala Gly Ile Gly Asn Leu Val Thr Phe Gly His Ser Leu Ser
             35                  40                  45

Lys Thr Cys Ser Pro Ala Cys Pro Ile Pro Glu Gly Val Asn Val Gly
         50                  55                  60

Val Ala Ser Met Gly Ile Ser Cys Cys Gln Ser Phe Leu Cys Asn Phe
 65                  70                  75                  80

Ser Ala Ala Asp Gly Gly Leu Arg Ala Ser Val Thr Leu Leu Gly Ala
                 85                  90                  95

Gly Leu Leu Leu Ser Leu Leu Pro Ala Leu Leu Arg Phe Gly Pro
                100                 105                 110

<210> SEQ ID NO 39
<211> LENGTH: 111
<212> TYPE: PRT
<213> ORGANISM: Macaca fascicularis

<400> SEQUENCE: 39

Leu Met Cys Phe Ser Cys Leu Asn Gln Lys Ser Asn Leu Tyr Cys Leu
 1               5                  10                  15

Lys Pro Thr Ile Cys Ser Asp Gln Asp Asn Tyr Cys Val Thr Val Ser
                 20                  25                  30

Thr Ser Ala Gly Ile Gly Asn Leu Val Thr Phe Gly His Ser Leu Ser
             35                  40                  45

Lys Thr Cys Ser Pro Ala Cys Pro Leu Pro Glu Gly Ile Asn Val Gly
         50                  55                  60

Val Ala Ser Met Gly Ile Ser Cys Cys Gln Ser Phe Leu Cys Asn Phe
 65                  70                  75                  80

Ser Ala Ala Asp Gly Gly Leu Arg Ala Ser Ala Thr Leu Leu Gly Ala
                 85                  90                  95

Gly Leu Leu Leu Ser Leu Leu Pro Ala Leu Leu Arg Phe Gly Pro
                100                 105                 110

<210> SEQ ID NO 40
<211> LENGTH: 111

```
<212> TYPE: PRT
<213> ORGANISM: Macaca mulatta

<400> SEQUENCE: 40

Leu Met Cys Phe Ser Cys Leu Asn Gln Lys Ser Asn Leu Tyr Cys Leu
1               5                   10                  15

Lys Pro Thr Ile Cys Ser Asp Gln Asp Asn Tyr Cys Val Thr Val Ser
            20                  25                  30

Thr Ser Ala Gly Ile Gly Asn Leu Val Thr Phe Gly His Ser Leu Ser
        35                  40                  45

Lys Thr Cys Ser Pro Ala Cys Pro Leu Pro Glu Gly Ile Asn Val Gly
    50                  55                  60

Val Ala Ser Met Gly Ile Ser Cys Cys Gln Ser Phe Leu Cys Asn Phe
65                  70                  75                  80

Ser Ala Ala Asp Gly Gly Leu Arg Ala Ser Ala Thr Leu Leu Gly Ala
                85                  90                  95

Gly Leu Leu Leu Ser Leu Leu Pro Ala Leu Leu Arg Phe Gly Pro
            100                 105                 110

<210> SEQ ID NO 41
<211> LENGTH: 110
<212> TYPE: PRT
<213> ORGANISM: Mus musculus

<400> SEQUENCE: 41

Leu Met Cys Phe Ser Cys Thr Asp Gln Lys Asn Asn Ile Asn Cys Leu
1               5                   10                  15

Trp Pro Val Ser Cys Gln Glu Lys Asp His Tyr Cys Ile Thr Leu Ser
            20                  25                  30

Ala Ala Ala Gly Phe Gly Asn Val Asn Leu Gly Tyr Thr Leu Asn Lys
        35                  40                  45

Gly Cys Ser Pro Ile Cys Pro Ser Glu Asn Val Asn Leu Asn Leu Gly
    50                  55                  60

Val Ala Ser Val Asn Ser Tyr Cys Cys Gln Ser Ser Phe Cys Asn Phe
65                  70                  75                  80

Ser Ala Ala Gly Leu Gly Leu Arg Ala Ser Ile Pro Leu Leu Gly Leu
                85                  90                  95

Gly Leu Leu Leu Ser Leu Leu Ala Leu Leu Gln Leu Ser Pro
            100                 105                 110

<210> SEQ ID NO 42
<211> LENGTH: 110
<212> TYPE: PRT
<213> ORGANISM: Rat rattus

<400> SEQUENCE: 42

Leu Met Cys Phe Ser Cys Thr Asp Gln Lys Asn Asn Ile Asn Cys Leu
1               5                   10                  15

Trp Pro Val Ser Cys Ser Ser Thr Asp Asn Tyr Cys Ile Thr Leu Ser
            20                  25                  30

Ala Ala Ala Gly Phe Gly Asn Val Asn Leu Gly Tyr Thr Leu Asn Lys
        35                  40                  45

Gly Cys Ser Pro Thr Cys Pro Arg Glu Asn Ile Asn Ile Asn Leu Gly
    50                  55                  60

Val Ala Ser Val Asn Ser Tyr Cys Cys Gln Ser Ser Phe Cys Asn Phe
65                  70                  75                  80

Ser Thr Ala Gly Leu Gly Leu Arg Ala Ser Ile Pro Leu Leu Gly Leu
```

85                  90                  95

Gly Leu Leu Ser Leu Leu Ala Val Leu Arg Leu Ser Pro
                100                 105                 110

<210> SEQ ID NO 43
<211> LENGTH: 120
<212> TYPE: PRT
<213> ORGANISM: Artificial sequence
<220> FEATURE:
<223> OTHER INFORMATION: Synthetic

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Gly Tyr
            20                  25                  30

Ser Val Asn Trp Val Arg Gln Ala Pro Gly Lys Gly Leu Glu Trp Val
        35                  40                  45

Gly Met Ile Trp Gly Asp Gly Ser Thr Asp Tyr Asn Ser Ala Leu Lys
    50                  55                  60

Ser Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Tyr Phe Asn Tyr Ala Ser Trp Phe Ala Tyr Trp Gly Gln
                100                 105                 110

Gly Thr Leu Val Thr Val Ser Ser
        115                 120

<210> SEQ ID NO 44
<211> LENGTH: 120
<212> TYPE: PRT
<213> ORGANISM: Artificial sequence
<220> FEATURE:
<223> OTHER INFORMATION: Synthetic

<400> SEQUENCE: 44

Gln Val Gln Leu Lys Glu Ser Gly Pro Gly Leu Val Ala Pro Ser Gln
1               5                   10                  15

Ser Leu Ser Leu Thr Cys Thr Val Ser Gly Phe Ser Leu Thr Gly Tyr
            20                  25                  30

Ser Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Thr Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Asp Tyr Tyr Phe Asn Tyr Ala Ser Trp Phe Ala Tyr Trp Gly Pro
                100                 105                 110

Gly Thr Leu Val Thr Val Ser Ala
        115                 120

<210> SEQ ID NO 45
<211> LENGTH: 21
<212> TYPE: DNA
<213> ORGANISM: Artificial sequence
<220> FEATURE:

```
<223> OTHER INFORMATION: Synthetic

<400> SEQUENCE: 45
gtgcctgatc tgtgcccttg g                                               21

<210> SEQ ID NO 46
<211> LENGTH: 20
<212> TYPE: DNA
<213> ORGANISM: Artificial sequence
<220> FEATURE:
<223> OTHER INFORMATION: Synthetic

<400> SEQUENCE: 46
cccggaagtg gcagaaaccc                                                 20

<210> SEQ ID NO 47
<211> LENGTH: 423
<212> TYPE: DNA
<213> ORGANISM: Artificial sequence
<220> FEATURE:
<223> OTHER INFORMATION: Synthetic

<400> SEQUENCE: 47
gtgcctgatc tgtgcccttg gtcccaggtc aggcccaccc cctgcacctc cacctgcccc     60
agcccctgcc tctgcccaag tgggccagct gccctcactt ctggggtgga tgatgtgacc    120
ttccttgggg gactgcggaa gggacgaggg ttccctggag tcttacggtc caacatcaga    180
ccaagtccca tggacatgct gacagggtcc cagggagac cgtgtcagta gggatgtgtg    240
cctggctgtg tacgtgggtg tgcagtgcac gtgagagcac gtggcggctt ctgggggcca    300
tgtttgggga gggaggtgtg ccagcagcct ggagagcctc agtccctgta gccccctgcc    360
ctggcacagc tgcatgcact tcaagggcag cctttggggg ttggggtttc tgccacttcc    420
ggg                                                                  423

<210> SEQ ID NO 48
<211> LENGTH: 19
<212> TYPE: DNA
<213> ORGANISM: Artificial sequence
<220> FEATURE:
<223> OTHER INFORMATION: Synthetic

<400> SEQUENCE: 48
agcggattct catggaaca                                                  19

<210> SEQ ID NO 49
<211> LENGTH: 18
<212> TYPE: DNA
<213> ORGANISM: Artificial sequence
<220> FEATURE:
<223> OTHER INFORMATION: Synthetic

<400> SEQUENCE: 49
ctggtcagcc aggagctt                                                   18

<210> SEQ ID NO 50
<211> LENGTH: 24
<212> TYPE: DNA
<213> ORGANISM: Artificial sequence
<220> FEATURE:
<223> OTHER INFORMATION: Synthetic

<400> SEQUENCE: 50
tccacaagct gaaggcagac aagg                                            24
```

```
<210> SEQ ID NO 51
<211> LENGTH: 19
<212> TYPE: DNA
<213> ORGANISM: Artificial sequence
<220> FEATURE:
<223> OTHER INFORMATION: Synthetic

<400> SEQUENCE: 51
agaaggcgtc aatgttggt                                               19

<210> SEQ ID NO 52
<211> LENGTH: 21
<212> TYPE: DNA
<213> ORGANISM: Artificial sequence
<220> FEATURE:
<223> OTHER INFORMATION: Synthetic

<400> SEQUENCE: 52
cactgaaatt gcacagaaag c                                            21

<210> SEQ ID NO 53
<211> LENGTH: 21
<212> TYPE: DNA
<213> ORGANISM: Artificial sequence
<220> FEATURE:
<223> OTHER INFORMATION: Synthetic

<400> SEQUENCE: 53
ttccatgggc atcagctgct g                                            21
```

US 10,889,651 B2

ANTI-LY6E ANTIBODIES AND METHODS OF USE

This application is a divisional of U.S. application Ser. No. 15/018,710, filed Feb. 8, 2016, which is a divisional of U.S. application Ser. No. 14/518,294, filed Oct. 20, 2014, which issued as U.S. Pat. No. 9,290,578, on Mar. 22, 2016, which claims the benefit of U.S. Provisional Application No. 61/893,553, filed Oct. 21, 2013, all of which are incorporated by reference herein in their entirety for any purpose.

REFERENCE TO SEQUENCE LISTING

A sequence listing is submitted concurrently with the specification as an ASCII formatted text file via EFS-Web, with a file name of "2018-07-31_01146-0031-02US_SeqList.txt", a creation date of Jul. 30, 2018, and a size of 26,927 bytes. The sequence listing filed via EFS-Web is part of the specification and is hereby incorporated by reference in its entirety.

FIELD OF THE INVENTION

The present invention relates to anti-Ly6E antibodies and immunoconjugates and methods of using the same.

BACKGROUND

Lymphocyte antigen 6 complex, locus E (Ly6E), also known as retinoic acid induced gene E (RIG-E) and stem cell antigen 2 (SCA-2). It is a GPI linked, 131 amino acid length, ~8.4 kDa protein of unknown function with no known binding partners. It was initially identified as a transcript expressed in immature thymocyte, thymic medullary epithelial cells in mice. RIG-E, a human homolog of the murine Ly-6 family, is induced by retinoic acid during the differentiation of acute promyelocytic leukemia cell.

Mao M., Yu M., Tong J.-H., Ye J., Zhu J., Huang Q.-H., Fu G., Yu L., Zhao S.-Y., Waxman S., Lanotte M., Wang Z.-Y., Tan J.-Z., Chan S.-J., Chen Z. Proc. Natl. Acad. Sci. U.S.A. 93:5910-5914 (1996).

There is a need in the art for agents that target Ly6E for the diagnosis and treatment of Ly6E-associated conditions, such as cancer. The invention fulfills that need and provides other benefits.

SUMMARY OF THE INVENTION

The invention provides anti-Ly6E antibodies, immunoconjugates and methods of using the same.

In some embodiments, an isolated antibody that binds to Ly6E is provided, wherein the antibody comprises (a) HVR-H3 comprising the amino acid sequence of SEQ ID NO:34, (b) HVR-L3 comprising the amino acid sequence of SEQ ID NO:31, and (c) HVR-H2 comprising the amino acid sequence of SEQ ID NO:33. In some embodiments, the antibody comprises (a) HVR-H1 comprising the amino acid sequence of SEQ ID NO:32, (b) HVR-H2 comprising the amino acid sequence of SEQ ID NO:33, and (c) HVR-H3 comprising the amino acid sequence of SEQ ID NO:34. In some embodiments, the antibody comprises (a) HVR-L1 comprising the amino acid sequence of SEQ ID NO:29; (b) HVR-L2 comprising the amino acid sequence of SEQ ID NO:30; and (c) HVR-L3 comprising the amino acid sequence of SEQ ID NO:31. In some embodiments, the antibody comprises (a) a VH sequence having at least 95% sequence identity to the amino acid sequence of SEQ ID NO:28; (b) a VL sequence having at least 95% sequence identity to the amino acid sequence of SEQ ID NO:27; or (c) a VH sequence as in (a) and a VL sequence as in (b). In some embodiments, the antibody comprises a VH sequence of SEQ ID NO:28. In some embodiments, the antibody comprises a VL sequence of SEQ ID NO:27.

In some embodiments, an isolated antibody that binds Ly6E is provided, wherein the antibody comprises a VH sequence of SEQ ID NO:28 and a VL sequence of SEQ ID NO:27.

In some embodiments, the antibody that binds Ly6E is a monoclonal antibody. In some embodiments, the antibody is a mouse, rabbit, human, humanized, or chimeric antibody. In some embodiments, the antibody is an IgG. In other embodiments, the IgG is an IgG1, IgG2a or IgG2b, or IgG3, or IgG4.

In some embodiments, an isolated nucleic acid encoding any of the antibodies described herein is provided. In some embodiments, a host cell comprising the isolated nucleic acid is provided. In some embodiments, a method of producing an antibody described herein is provided, comprising culturing the host cell.

In some embodiments, an immuneconjugate comprising an antibody described herein and a cytotoxic agent is provided. In some embodiments, a pharmaceutical composition comprising the immunoconjugate and a pharmaceutically acceptable carrier is provided.

In some embodiments, an antibody described herein is conjugated to a label. In some embodiments, the label is a positron emitter. In some such embodiments, the positron emitter is $^{89}$Zr.

In some embodiments, methods of detecting human Ly6E in a biological sample are provided. In some embodiments, the method comprises contacting the biological sample with an anti-Ly6E antibody described herein under conditions permissive for binding of the anti-Ly6E antibody to a naturally occurring human Ly6E. In some embodiments, the method comprises detecting whether a complex is formed between the anti-Ly6E antibody and a naturally occurring human Ly6E in the biological sample. In some embodiments, the biological sample is a breast cancer sample, a pancreatic cancer sample, a colon cancer sample, a colorectal cancer sample, melanoma cancer sample, ovarian cancer sample, a non-small cell lung cancer sample, an esophageal cancer sample, a head and neck cancer sample, a kidney cancer sample, a soft tissue cancer sample, an endometrial cancer sample, or a gastric cancer sample.

In some embodiments, methods of detecting a Ly6E-positive cancer are provided. In some embodiments, the method comprises (i) administering a labeled anti-Ly6E antibody to a subject having or suspected of having a Ly6E-positive cancer, wherein the labeled anti-Ly6E antibody comprises an anti-Ly6E antibody described herein, and (ii) detecting the labeled anti-Ly6E antibody in the subject. In some embodiments, detection of the labeled anti-Ly6E antibody indicates a Ly6E-positive cancer in the subject. In some embodiments, the labeled anti-Ly6E antibody comprises an anti-Ly6E antibody described herein conjugated to a positron emitter. In some such embodiments, the positron emitter is $^{89}$Zr.

In some embodiments, a method of identifying a cancer patient as having a Ly6E-positive cancer is provided. In some embodiments, the method comprises contacting a cancer sample from the patient with an anti-Ly6E antibody described herein under conditions permissive for binding of the anti-Ly6E antibody to a naturally occurring human Ly6E. In some embodiments, the method comprises detecting whether a complex is formed between the anti-Ly6E antibody and a naturally occurring human Ly6E in the cancer sample. In some embodiments, the cancer patient is identified as having a Ly6E-positive cancer if a complex is between the anti-Ly6E antibody described herein and a naturally occurring human Ly6E in the cancer biopsy sample is detected.

In some embodiments, methods of selecting a cancer patient for treatment with an immunoconjugate comprising an anti-Ly6E antibody are provided. In some embodiments, the method comprises contacting a cancer sample from the patient with an anti-Ly6E antibody described herein under conditions permissive for binding of the anti-Ly6E antibody to a naturally occurring human Ly6E. In some embodiments, the method comprises detecting whether a complex is formed between the anti-Ly6E antibody and a naturally occurring human Ly6E in the cancer sample. In some embodiments, the cancer patient is selected if a complex is between the anti-Ly6E antibody and a naturally occurring human Ly6E in the cancer biopsy sample is detected. In some such embodiments, the cancer patient is selected for treatment with an immunoconjugate comprising an anti-Ly6E antibody comprising (a) HVR-H1 comprising the amino acid sequence of SEQ ID NO:10, (b) HVR-H2 comprising the amino acid sequence of SEQ ID NO:11, (c) HVR-H3 comprising the amino acid sequence of SEQ ID NO:12, (d) HVR-L1 comprising the amino acid sequence of SEQ ID NO:7; (e) HVR-L2 comprising the amino acid sequence of SEQ ID NO:8; and (f) HVR-L3 comprising the amino acid sequence of SEQ ID NO:9. In some embodiments, the cancer patient is selected for treatment with an immunoconjugate comprising an anti-Ly6E antibody comprising a VH sequence of SEQ ID NO:5 and a VL sequence of SEQ ID NO:3. In some embodiments, the immunoconjugate comprises an anti-Ly6E antibody conjugated to a cytotoxic agent. In some embodiments, the cancer sample is a breast cancer sample, a pancreatic cancer sample, a colon cancer sample, a colorectal cancer sample, melanoma cancer sample, ovarian cancer sample, a non-small cell lung cancer sample, an esophageal cancer sample, a head and neck cancer sample, a kidney cancer sample, a soft tissue cancer sample, an endometrial cancer sample, or a gastric cancer sample. In some embodiments, the breast cancer sample is from a Her2 positive breast cancer, a Her2 negative breast cancer, a Her2 negative/hormone receptor positive (Her2−/ER+/PR+) breast cancer, or a triple negative (Her2−/ER−/PR−) breast cancer. In some embodiments, the gastric cancer sample is from a Her2 positive gastric cancer or a Her2 negative gastric cancer.

BRIEF DESCRIPTION OF THE FIGURES

Figure 1:
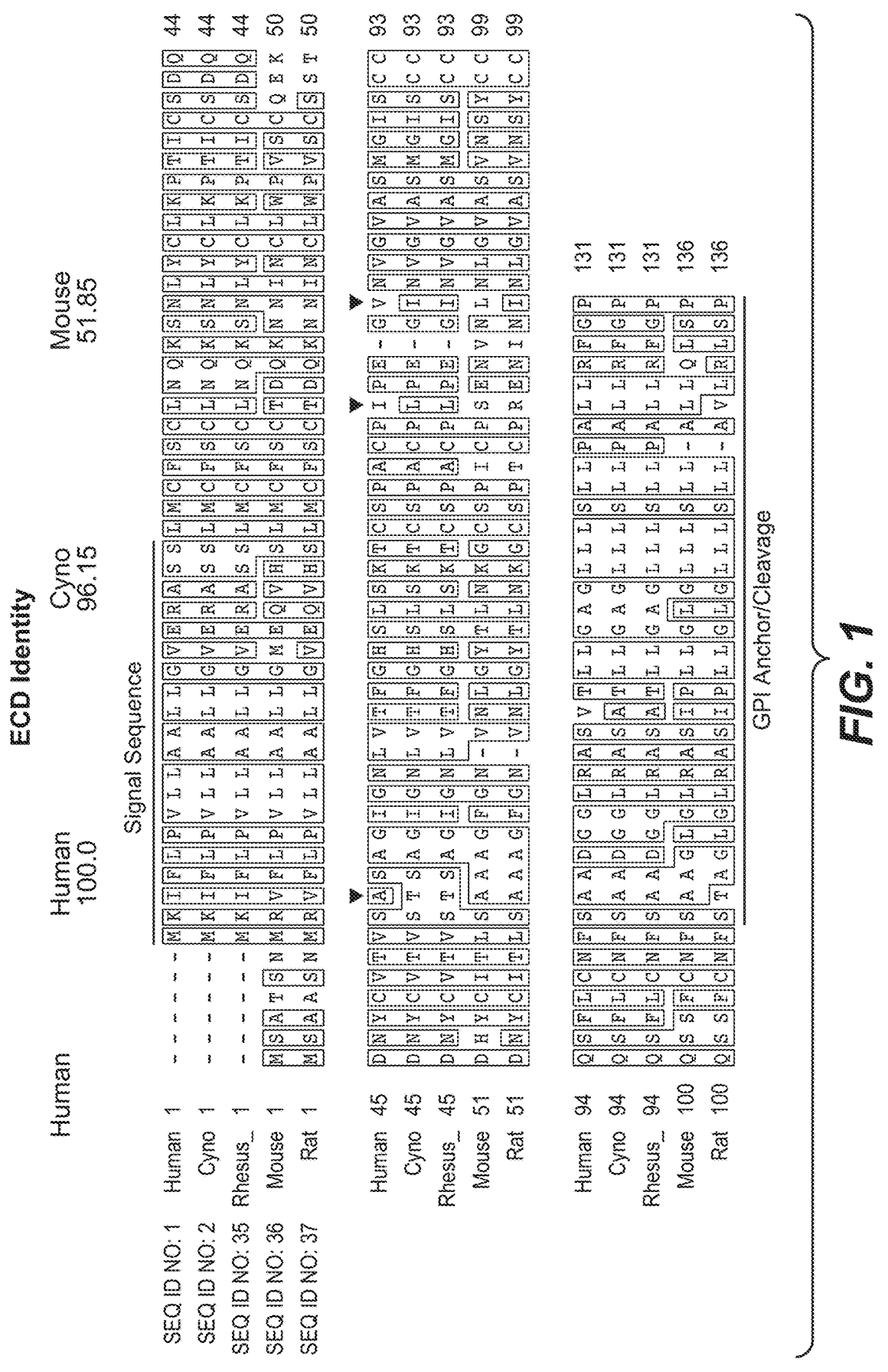

FIG. 1 shows a sequence alignment comparing the sequences of Ly6E orthologs from human (SEQ ID NO: 1), Cynomolgus monkey (SEQ ID NO: 2), Rhesus (SEQ ID NO: 35), mouse (SEQ ID NO: 36), and rat species (SEQ ID NO: 37). The percent identity at the amino acid level between these sequences in the extracellular domain (ECD) is shown to be ~96% between human and cynomolgus monkey Ly6E and ~52% between human and rat Ly6E.

FIG. 4 shows the light chain variable domain sequence and the heavy chain variable domain sequence of rabbit anti-Ly6E antibody clone GEN-93-8-1. Hypervariable regions (HVRs) are underlined. Positions are numbered according to Kabat.

FIGS. 8A-E show the in vivo efficacy of anti-Ly6E ADC, as described in FIG. 5, in primary triple-negative (Her2−/ER−/PR−) breast cancer tumor xenograft model HBCx-8 established at XenTech (Evry, France). Panel A shows subcutaneous tumors established in immunodeficient mice implanted with patient derived breast cancer tumor material. When tumor volumes reached approximately 100-250 mm$^3$ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various XenTech primary tumor models and in HCC1569 X1 and SU.86.86 cell lysates by immunoblotting with mouse anti-Ly6E antibody 4D8. Total β-Actin protein levels were measured in parallel to serve as loading controls. Panel C shows Ly6E staining on HBCx-8 tumors by immunohistochemistry using mouse anti-Ly6E clone 10G7.7.8. Panel D shows 1+/2+Ly6E staining on HBCx-8 tumors by immunohistochemistry using rabbit anti-Ly6E antibody clone GEN-93-8-1. Independent staining of multiple tumor samples showed staining patterns at a 1+ or 2+ level using 10G7.7.8 or GEN-93-8-1, however the staining with GEN-93-8-1 was more robust and homogenous as compared to 10G7.7.8 staining. Panel E shows total Ly6E protein expression in HBCx-8 cell lysates by immunoblotting with antibody GEN-93-8-1. GAPDH protein levels were measured in parallel to serve as loading controls.

DETAILED DESCRIPTION OF EMBODIMENTS OF THE INVENTION

I. Definitions

Figure 2:
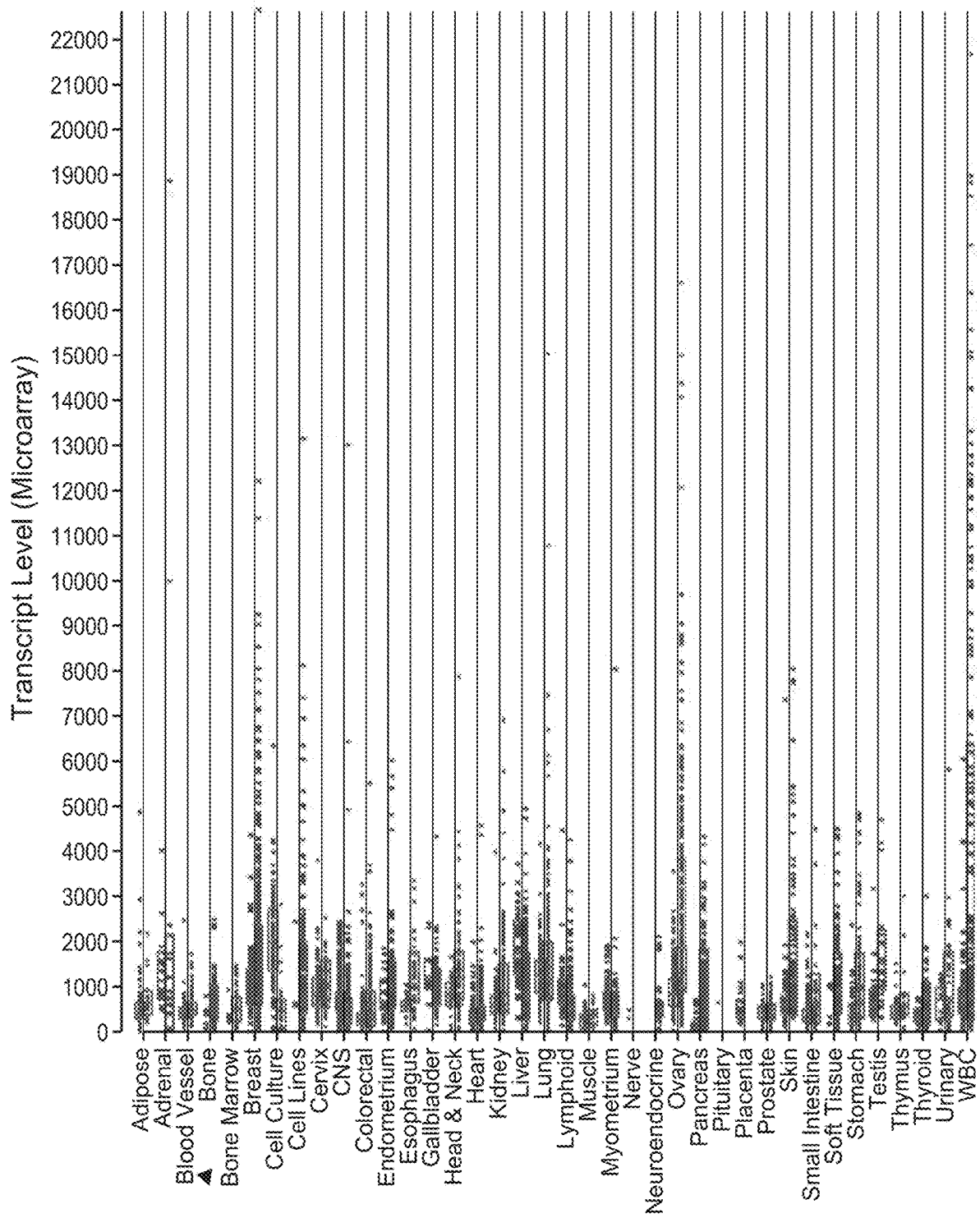
FIG. 2 shows a Genelogic profile of Ly6E mRNA expression as further described in Example 1. Measurements were carried out on the Affymetrix U133P chip and are expressed as scaled average differences in Ly6E expression in human tissues. Each dot represents a normal (green), tumor (red), or diseased non-tumor (blue) human tissue specimen. Rectangles encompass the 25 to 75 percentile range for each distribution. WBC=white blood cells. Over-expression of Ly6E is seen in breast, pancreatic, colorectal, lung, melanoma and ovarian cancers, among others.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Ly6E antibody" and "an antibody that binds to Ly6E" refer to an antibody that is capable of binding Ly6E with sufficient affinity such that the antibody is useful as a diagnostic and/or therapeutic agent in targeting Ly6E. In one embodiment, the extent of binding of an anti-Ly6E antibody to an unrelated, non-Ly6E protein is less than about 10% of the binding of the antibody to Ly6E as measured, e.g., by a radioimmunoassay (RIA) or by scatchard analysis or by surface plasmon resonance, such as, for example, Biacore. In certain embodiments, an antibody that binds to Ly6E has a dissociation constant (Kd) of ≤1 μM, ≤100 nM, ≤10 nM, ≤1 nM, ≤0.1 nM, ≤0.01 nM, or <0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Ly6E antibody binds to an epitope of Ly6E that is conserved among Ly6E from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term "antibody drug conjugate" (ADC) as used herein is equivalent to the term "immunoconjugate".

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include a cancer that over-expresses Ly6E, which may include, for example, breast cancer and/or metastatic breast cancer, including Her2 positive breast cancer, Her2 negative breast cancers, Her2 negative/hormone receptor positive (Her2–/ER+/PR+), and triple negative breast cancers, pancreatic cancer and/or metastatic pancreatic cancer, colon cancer, colorectal cancer, skin cancer, melanoma and/or metastatic melanoma, ovarian cancer, non-small cell lung cancer (squamous and/or non-squamous, such as adenocarcinoma), gastric cancer, including Her2 positive gastric cancer and/or Her2 negative gastric cancer, squamous cell cancer, small-cell lung cancer, adenocarcinoma of the lung, squamous carcinoma of the lung, cancer of the peritoneum, hepatocellular cancer, gastrointestinal cancer, glioma, cervical cancer, liver cancer, bladder cancer, hepatoma, soft tissue cancer, endometrial or uterine carcinoma, salivary gland carcinoma, esophageal cancer, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The term "cytotoxic agent" as used herein refers to a substance that inhibits or prevents a cellular function and/or causes cell death or destruction. Cytotoxic agents include, but are not limited to, radioactive isotopes (e.g., $At_{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "rabbit antibody" is one which possesses an amino acid sequence which corresponds to that of an antibody produced by a rabbit or a rabbit cell or derived from a non-rabbit source that utilizes rabbit antibody repertoires or other rabbit antibody-encoding sequences.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent. An immunoconjugate is equivalent to the term "antibody drug conjugate" (ADC).

An "individual" or "patient" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Ly6E antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "Ly6E," as used herein, refers to any native, mature Ly6E which results from processing of a Ly6E precursor protein in a cell. The term includes Ly6E from any vertebrate source, including mammals such as primates (e.g. humans and cynomolgus or rhesus monkeys) and rodents (e.g., mice and rats), unless otherwise indicated. The term also includes naturally occurring variants of Ly6E, e.g., splice variants or allelic variants. The amino acid sequence of an exemplary human Ly6E precursor protein, with signal sequence (amino acids 1-20=signal sequence) is shown in SEQ ID NO: 1. The amino acid sequence of an exemplary mature human Ly6E is shown in SEQ ID NO: 38. The sequence for amino acids 1-131 of an exemplary cynomolgous monkey Ly6E is shown in SEQ ID NO: 2. The amino acid sequence of an exemplary mature cynomologous Ly6E is shown in SEQ ID NO: 39. The amino acid sequence for an exemplary rat Ly6E precursor (with signal sequence, amino acids 1-26) and mature sequences are shown in SEQ ID NOs: 37 and 42, respectively. The amino acid sequences for exemplary mouse Ly6E precursor (with signal sequence, amino acids 1-26) and mature sequences are shown in SEQ ID NOS: 36 and 41, respectively. The amino acid sequences for exemplary rhesus Ly6E precursor (with signal sequence, amino acids 1-20) and mature sequences are shown in SEQ ID NOs: 35 and 40, respectively.

The term "Ly6E-positive cancer" refers to a cancer comprising cells that express Ly6E on their surface. For the purposes of determining whether a cell expresses Ly6E on the surface, Ly6E mRNA expression is considered to correlate to Ly6E expression on the cell surface. In some embodiments, expression of Ly6E mRNA is determined by a method selected from in situ hybridization and RT-PCR (including quantitative RT-PCR). Alternatively, expression of Ly6E on the cell surface can be determined, for example, using antibodies to Ly6E in a method such as immunohistochemistry, FACS, etc. In some embodiments, a Ly6E-positive cancer includes breast cancer and metastatic breast cancer, including Her2 positive breast cancers, Her2 negative breast cancers, Her2 negative/hormone receptor positive (Her2−/ER+/PR+), and triple negative breast cancers, pancreatic cancer, colon cancer, colorectal cancer, melanoma, ovarian cancer, lung cancer, non-small cell lung cancer (squamous and/or non-squamous, such as adenocarcinoma), soft tissue cancer, endometrial cancer, esophageal cancer, head and neck cancer, kidney cancer, or gastric cancer, including Her2 positive gastric cancer and Her2 negative gastric cancer, in each case exhibiting a detectable level of Ly6E expression.

The term "Ly6E-positive cell" refers to a cancer cell that expresses Ly6E on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

A "platinum complex" as used herein refers to anti-cancer chemotherapy drugs such as, for example, but not limited to, cisplatin, oxaliplatin, carboplatin, iproplatin, satraplatin, CI-973, AZ0473, DWA2114R, nedaplatin, and sprioplatin, which exert efficacy against tumors based on their ability to covalently bind to DNA.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on antibodies that bind to Ly6E and immunoconjugates comprising such antibodies. Antibodies and immunoconjugates of the invention are useful, e.g., for the diagnosis or treatment of Ly6E-positive cancers.

A. Exemplary Anti-Ly6E Antibodies

In some embodiments, the invention provides isolated antibodies that bind to Ly6E. In certain embodiments, an anti-Ly6E antibody has at least one or more of the following characteristics, in any combination:
(a) binds to an epitope within amino acids 21-131 of SEQ ID NO: 1; and
(b) binds Ly6E with an affinity of ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM as measured by either SPR or scatchard analysis.

Antibody 9B12

A nonlimiting exemplary anti-Ly6E antibody is the murine 9B12 and humanized variants thereof, such as, for example, hu9B12.v12 (see, e.g., variable region sequences shown in SEQ ID NOs: 4 and 6; and SEQ ID NOs: 3 and 5). In some embodiments, Ly6E is human Ly6E. In some embodiments, Ly6E is selected from human, cynomolgus monkey, rhesus monkey, mouse or rat Ly6E.

In some embodiments, an anti-Ly6E antibody binds to an epitope within amino acids 21-131 of SEQ ID NO: 1. In some such embodiments, the anti-Ly6E antibody binds Ly6E with an affinity of ≤7 nM, or ≤6 nM, or ≤5 nM, or ≤4 nM, or ≤3 nM, or ≤2 nM, or ≤1 nM, and optionally ≥0.0001 nM, or ≥0.001 nM, or ≥0.01 nM as measured by either SPR or scatchard analysis. A nonlimiting exemplary antibody of the invention is the murine 9B12 and humanized variants thereof, such as, for example, hu9B12.v12. In some embodiments, Ly6E is human Ly6E. In some embodiments, Ly6E is human Ly6E or cynomolgus monkey Ly6E.

In one aspect, the invention provides an anti-Ly6E antibody comprising at least one, two, three, four, five, or six HVRs selected from (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:7; (e) HVR-L2 comprising the amino acid sequence of SEQ ID NO:8; and (f) HVR-L3 comprising the amino acid sequence of SEQ ID NO:9.

In one aspect, the invention provides an antibody comprising at least one, at least two, or all three VH HVR sequences selected from (a) HVR-H1 comprising the amino acid sequence of SEQ ID NO:10; (b) HVR-H2 comprising the amino acid sequence of SEQ ID NO:11; and (c) HVR-H3 comprising the amino acid sequence of SEQ ID NO:12. In one embodiment, the antibody comprises HVR-H3 comprising the amino acid sequence of SEQ ID NO:12. In another embodiment, the antibody comprises HVR-H3 comprising the amino acid sequence of SEQ ID NO:12 and HVR-L3 comprising the amino acid sequence of SEQ ID NO:9. In a further embodiment, the antibody comprises HVR-H3 comprising the amino acid sequence of SEQ ID NO:12, HVR-L3 comprising the amino acid sequence of SEQ ID NO:9, and HVR-H2 comprising the amino acid sequence of SEQ ID NO:11. In a further embodiment, the antibody comprises (a) HVR-H1 comprising the amino acid sequence of SEQ ID NO:10; (b) HVR-H2 comprising the amino acid sequence of SEQ ID NO:11; and (c) HVR-H3 comprising the amino acid sequence of SEQ ID NO:12.

In another aspect, the invention provides an antibody comprising at least one, at least two, or all three VL HVR sequences selected from (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9. In one embodiment, the antibody comprises (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9.

In another aspect, an antibody of the invention comprises (a) a VH domain comprising at least one, at least two, or all three VH HVR sequences selected from (i) HVR-H1 comprising the amino acid sequence of SEQ ID NO:10, (ii) HVR-H2 comprising the amino acid sequence of SEQ ID NO:11, and (iii) HVR-H3 comprising an amino acid sequence selected from SEQ ID NO:12; and (b) a VL domain comprising at least one, at least two, or all three VL HVR sequences selected from (i) HVR-L1 comprising the amino acid sequence of SEQ ID NO:7, (ii) HVR-L2 comprising the amino acid sequence of SEQ ID NO:8, and (c) HVR-L3 comprising the amino acid sequence of SEQ ID NO:9.

In another aspect, the invention provides an antibody comprising (a) HVR-H1 comprising the amino acid sequence of SEQ ID NO:10; (b) HVR-H2 comprising the amino acid sequence of SEQ ID NO:11; (c) HVR-H3 comprising the amino acid sequence of SEQ ID NO:12; (d) HVR-L1 comprising the amino acid sequence of SEQ ID NO:7; (e) HVR-L2 comprising the amino acid sequence of SEQ ID NO:8; and (f) HVR-L3 comprising an amino acid sequence selected from SEQ ID NO:9.

In any of the above embodiments, an anti-Ly6E antibody is humanized. In one embodiment, an anti-Ly6E antibody comprises HVRs as in any of the above embodiments, and further comprises an acceptor human framework, e.g. a human immunoglobulin framework or a human consensus framework. In another embodiment, an anti-Ly6E antibody comprises HVRs as in any of the above embodiments, and it further comprises a light chain variable domain framework FR2 sequence of SEQ ID NO:20 or light chain variable domain framework FR3 of SEQ ID NO:21 or heavy chain variable domain framework FR1 or SEQ ID NO:23, or heavy chain variable domain framework FR2 of SEQ ID NO:24.

In another aspect, an anti-Ly6E antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:5. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:5. In certain embodiments, substitutions, insertions, or deletions occur in regions outside the HVRs (i.e., in the FRs). Optionally, the anti-Ly6E antibody comprises the VH sequence in SEQ ID NO:5, including post-translational modifications of that sequence. In a particular embodiment, the VH comprises one, two or three HVRs selected from: (a) HVR-H1 comprising the amino acid sequence of SEQ ID NO:10, (b) HVR-H2 comprising the amino acid sequence of SEQ ID NO:11, and (c) HVR-H3 comprising the amino acid sequence of SEQ ID NO:12.

In another aspect, an anti-Ly6E antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:3. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:3. In certain embodiments, the substitutions, insertions, or deletions occur in regions outside the HVRs (i.e., in the FRs). Optionally, the anti-Ly6E antibody comprises the VL sequence in SEQ ID NO:3, including post-translational modifications of that sequence. In a particular embodiment, the VL comprises one, two or three HVRs selected from (a) HVR-L1 comprising the amino acid sequence of SEQ ID NO:7; (b) HVR-L2 comprising the amino acid sequence of SEQ ID NO:8; and (c) HVR-L3 comprising the amino acid sequence of SEQ ID NO:9.

In another aspect, an anti-Ly6E antibody is provided, wherein the antibody comprises a VH as in any of the embodiments provided above, and a VL as in any of the embodiments provided above. In one embodiment, the antibody comprises the VH and VL sequences in SEQ ID NO:5 and SEQ ID NO:3, respectively, including post-translational modifications of those sequences.

In a further aspect, the invention provides an antibody that binds to the same epitope as an anti-Ly6E antibody provided herein. For example, in certain embodiments, an antibody is provided that binds to the same epitope as an anti-Ly6E antibody comprising a VH sequence of SEQ ID NO:5 and a VL sequence of SEQ ID NO:3. In certain embodiments, an antibody is provided that binds to an epitope within a fragment of Ly6E consisting of amino acids 21-131 of SEQ ID NO:1.

In a further aspect of the invention, an anti-Ly6E antibody according to any of the above embodiments is a monoclonal antibody, including a chimeric, humanized or human antibody. In one embodiment, an anti-Ly6E antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-Ly6E antibody according to any of the above embodiments may incorporate any of the features, singly or in combination, as described in Sections 1-7 below.

Antibody GEN-93-8-1

Figure 4:
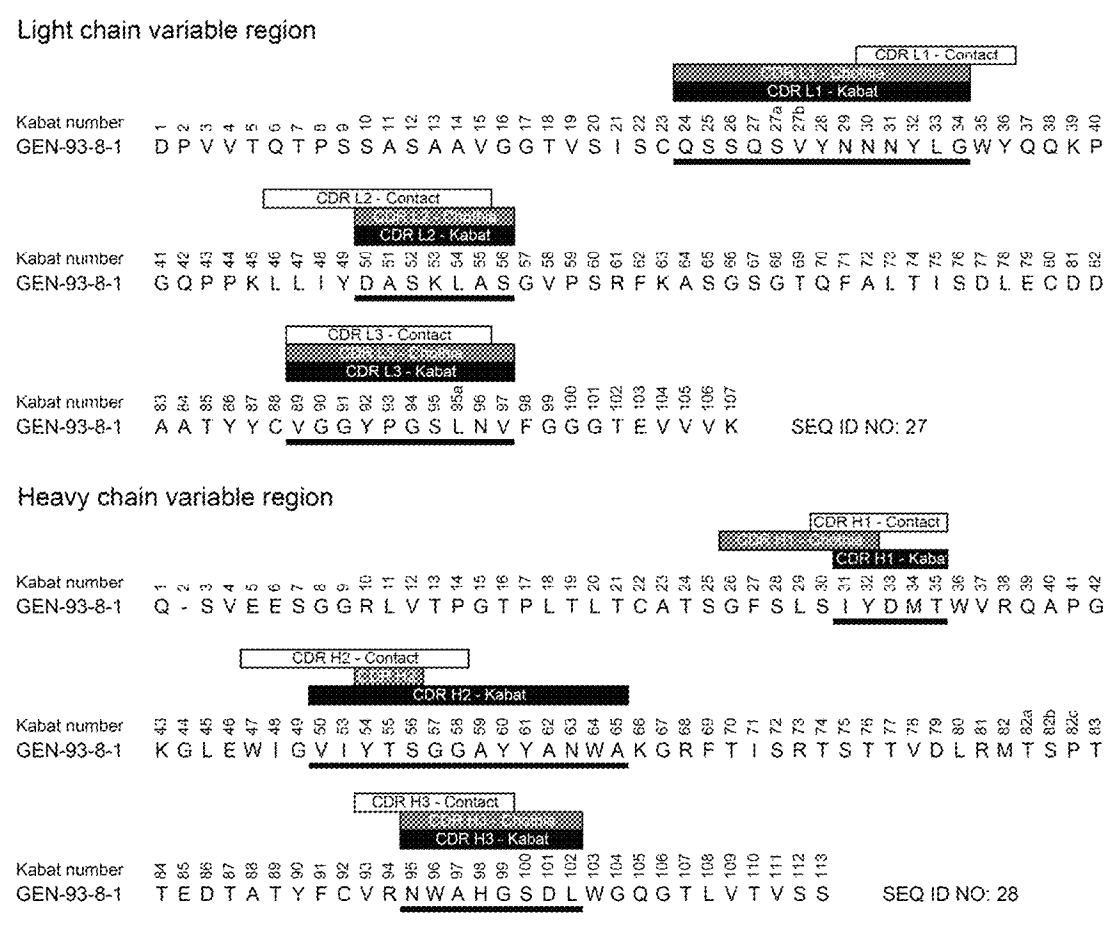

A nonlimiting exemplary anti-Ly6E antibody is the rabbit GEN-93-8-1 as shown in FIG. 4 and antibodies comprising one or more HVRs of GEN-93-8-1. In some embodiments, Ly6E is human Ly6E. In some embodiments, Ly6E is selected from human, non-human primate, mouse or rat Ly6E. In some embodiments, non-human primate Ly6E is cynomolgus monkey or rhesus monkey Ly6E.

In one aspect, the invention provides an anti-Ly6E antibody comprising at least one, two, three, four, five, or six HVRs selected from (a) HVR-H1 comprising the amino acid sequence of SEQ ID NO:32; (b) HVR-H2 comprising the amino acid sequence of SEQ ID NO:33; (c) HVR-H3 comprising the amino acid sequence of SEQ ID NO:34; (d) HVR-L1 comprising the amino acid sequence of SEQ ID NO:29; (e) HVR-L2 comprising the amino acid sequence of SEQ ID NO:30; and (f) HVR-L3 comprising the amino acid sequence of SEQ ID NO:31.

In one aspect, the invention provides an antibody comprising at least one, at least two, or all three VH HVR sequences selected from (a) HVR-H1 comprising the amino acid sequence of SEQ ID NO:32; (b) HVR-H2 comprising the amino acid sequence of SEQ ID NO:33; and (c) HVR-H3 comprising the amino acid sequence of SEQ ID NO:34. In one embodiment, the antibody comprises HVR-H3 comprising the amino acid sequence of SEQ ID NO:34. In another embodiment, the antibody comprises HVR-H3 comprising the amino acid sequence of SEQ ID NO:34 and HVR-L3 comprising the amino acid sequence of SEQ ID NO:31. In a further embodiment, the antibody comprises HVR-H3 comprising the amino acid sequence of SEQ ID NO:34, HVR-L3 comprising the amino acid sequence of SEQ ID NO:31, and HVR-H2 comprising the amino acid sequence of SEQ ID NO:33. In a further embodiment, the antibody comprises (a) HVR-H1 comprising the amino acid sequence of SEQ ID NO:32; (b) HVR-H2 comprising the amino acid sequence of SEQ ID NO:33; and (c) HVR-H3 comprising the amino acid sequence of SEQ ID NO:34.

In another aspect, the invention provides an antibody comprising at least one, at least two, or all three VL HVR sequences selected from (a) HVR-L1 comprising the amino acid sequence of SEQ ID NO:29; (b) HVR-L2 comprising the amino acid sequence of SEQ ID NO:30; and (c) HVR-L3 comprising the amino acid sequence of SEQ ID NO:31. In one embodiment, the antibody comprises (a) HVR-L1 comprising the amino acid sequence of SEQ ID NO:29; (b) HVR-L2 comprising the amino acid sequence of SEQ ID NO:30; and (c) HVR-L3 comprising the amino acid sequence of SEQ ID NO:31.

In another aspect, an antibody of the invention comprises (a) a VH domain comprising at least one, at least two, or all three VH HVR sequences selected from (i) HVR-H1 comprising the amino acid sequence of SEQ ID NO:32, (ii) HVR-H2 comprising the amino acid sequence of SEQ ID NO:33, and (iii) HVR-H3 comprising an amino acid sequence selected from SEQ ID NO:34; and (b) a VL domain comprising at least one, at least two, or all three VL HVR sequences selected from (i) HVR-L1 comprising the amino acid sequence of SEQ ID NO:29, (ii) HVR-L2 comprising the amino acid sequence of SEQ ID NO:30, and (c) HVR-L3 comprising the amino acid sequence of SEQ ID NO:31.

In another aspect, the invention provides an antibody comprising (a) HVR-H1 comprising the amino acid sequence of SEQ ID NO:32; (b) HVR-H2 comprising the amino acid sequence of SEQ ID NO:33; (c) HVR-H3 comprising the amino acid sequence of SEQ ID NO:34; (d) HVR-L1 comprising the amino acid sequence of SEQ ID NO:29; (e) HVR-L2 comprising the amino acid sequence of SEQ ID NO:30; and (f) HVR-L3 comprising an amino acid sequence selected from SEQ ID NO:31.

In any of the above embodiments, an anti-Ly6E antibody is humanized. In one embodiment, an anti-Ly6E antibody comprises HVRs as in any of the above embodiments, and further comprises an acceptor human framework, e.g. a human immunoglobulin framework or a human consensus framework.

In another aspect, an anti-Ly6E antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:28. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:28. In certain embodiments, substitutions, insertions, or deletions occur in regions outside the HVRs (i.e., in the FRs). Optionally, the anti-Ly6E antibody comprises the VH sequence in SEQ ID NO:28, including post-translational modifications of that sequence. In a particular embodiment, the VH comprises one, two or three HVRs selected from: (a) HVR-H1 comprising the amino acid sequence of SEQ ID NO:32, (b) HVR-H2 comprising the amino acid sequence of SEQ ID NO:33, and (c) HVR-H3 comprising the amino acid sequence of SEQ ID NO:34.

In another aspect, an anti-Ly6E antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:27. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Ly6E antibody comprising that sequence retains the ability to bind to Ly6E. In certain embodiments, a total of 1 to 10 amino acids have been substituted, inserted and/or deleted in SEQ ID NO:27. In certain embodiments, the substitutions, insertions, or deletions occur in regions outside the HVRs (i.e., in the FRs). Optionally, the anti-Ly6E antibody comprises the VL sequence in SEQ ID NO:27, including post-translational modifications of that sequence. In a particular embodiment, the VL comprises one, two or three HVRs selected from (a) HVR-L1 comprising the amino acid sequence of SEQ ID NO:29; (b) HVR-L2 comprising the amino acid sequence of SEQ ID NO:30; and (c) HVR-L3 comprising the amino acid sequence of SEQ ID NO:31.

In another aspect, an anti-Ly6E antibody is provided, wherein the antibody comprises a VH as in any of the embodiments provided above, and a VL as in any of the embodiments provided above. In one embodiment, the antibody comprises the VH and VL sequences in SEQ ID NO:28 and SEQ ID NO:27, respectively, including post-translational modifications of those sequences.

In a further aspect, the invention provides an antibody that binds to the same epitope as an anti-Ly6E antibody provided herein. For example, in certain embodiments, an antibody is provided that binds to the same epitope as an anti-Ly6E antibody comprising a VH sequence of SEQ ID NO:28 and a VL sequence of SEQ ID NO:27.

In a further aspect of the invention, an anti-Ly6E antibody according to any of the above embodiments is a monoclonal antibody, including a chimeric, humanized or human antibody. In one embodiment, an anti-Ly6E antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

In a further aspect, an anti-Ly6E antibody according to any of the above embodiments may incorporate any of the features, singly or in combination, as described in Sections 1-7 below.

Assays

To determine whether an anti-Ly6E antibody "binds to an epitope within amino acids 21-131 of SEQ ID NO: 1 Ly6E polypeptides with N- and C-terminal deletions are expressed in 293 cells and binding of the antibody to the truncated polypeptides is tested by FACS, wherein a substantial reduction (≥70% reduction) or elimination of binding of the antibody to a truncated polypeptide relative to binding to full-length Ly6E expressed in 293 cells indicates that the antibody does not bind to that truncated polypeptide.

Whether an anti-Ly6E antibody "binds with an affinity of ≤6 nM, or ≤5 nM, or ≤4 nM, or ≤3 nM, or ≤2 nM, or ≤1 nM," is determined according to a scatchard analysis as described herein in Example 4. Alternatively, an anti-Ly6E antibody affinity can be determined according to, for example, a BIAcore assay. Specifically, Kd is measured using surface plasmon resonance assays using a BIACORE®-3000 (BIAcore, Inc., Piscataway, N.J.). BIAcore™ research grade CM5 chips are activated with 1-ethyl-3-(3-dimethylaminopropyl) carbodiimide (EDC) and N-hydroxysuccinimide (NHS) reagents according to the supplier's instructions. Goat anti-human Fc IgGs are coupled to the chips to achieve approximately 10,000 response units (RU) in each flow cell. Unreacted coupling groups are blocked with 1M ethanolamine. For kinetics measurements, anti-Ly6E antibodies are captured to achieve approximately 300 RU. Two-fold serial dilutions of human Ly6E (for example, amino acids 21-131 fused to His-Fc expressed in a baculovirus system, or amino acids 21-131 fused to Fc expressed from CHO cells; 125 nM to 0.49 nM) are injected in HBS-P buffer (0.01 M HEPES pH7.4, 0.15 M NaCl, 0.005% surfactant P20) at 25° C. with a flow rate of 30 µl/min. Association rates ($k_{on}$) and dissociation rates ($k_{off}$) are calculated using a 1:1 Langmuir binding model (BIAcore™ Evaluation Software version 3.2). The equilibrium dissociation constant (Kd) is calculated as the ratio $k_{off}/k_{on}$. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLMAminco® spectrophotometer (ThermoSpectronic) with a stirred cuvette.

In any of the above embodiments, an anti-Ly6E antibody is humanized. In one embodiment, an anti-Ly6E antibody comprises HVRs as in any of the above embodiments, and further comprises a human acceptor framework, e.g. a human immunoglobulin framework or a human consensus framework. In certain embodiments, the human acceptor framework is the human VL kappa IV consensus (VLKiv) framework and/or the VH framework $VH_1$.

In a further aspect of the invention, an anti-Ly6E antibody according to any of the above embodiments is a monoclonal antibody, including a chimeric, humanized or human antibody. In one embodiment, an anti-Ly6E antibody is an antibody fragment, e.g., a Fv, Fab, Fab', scFv, diabody, or $F(ab')_2$ fragment. In another embodiment, the antibody is a substantially full length antibody, e.g., an IgG1 antibody or other antibody class or isotype as defined herein.

In a further aspect, an anti-Ly6E antibody according to any of the above embodiments may incorporate any of the features, singly or in combination, as described in Sections 1-7 below.

In a further aspect of the invention, an anti-Ly6E antibody according to any of the above embodiments is a monoclonal antibody, including a human antibody. In one embodiment, an anti-Ly6E antibody is an antibody fragment, e.g., a Fv, Fab, Fab', scFv, diabody, or $F(ab')_2$ fragment. In another embodiment, the antibody is a substantially full length antibody, e.g., an IgG2a antibody or other antibody class or isotype as defined herein.

In a further aspect, an anti-Ly6E antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM, and optionally is ≥$10^{-13}$ M. (e.g. $10^{-8}$ M or less, e.g. from $10^{-8}$ M to $10^{-13}$ M, e.g., from $10^{-9}$M to $10^{13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using scatchard analysis, as described in Example 4. According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol.*

Biol. 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. Nat. Med. 9:129-134 (2003). For a review of scFv fragments, see, e.g., Pluckthfin, in The Pharmacology of Monoclonal Antibodies, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., Nat. Med. 9:129-134 (2003); and Hollinger et al., Proc. Natl. Acad. Sci. USA 90: 6444-6448 (1993). Triabodies and tetrabodies are also described in Hudson et al., Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing SDR (a-CDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3562 (2006).

Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3): 185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J.,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Ly6E and the other is for any other antigen. In certain embodiments, one of the binding specificities is for Ly6E and the other is for CD3. See, e.g., U.S. Pat. No. 5,821,337. In certain embodiments, bispecific antibodies may bind to two different epitopes of Ly6E. Bispecific antibodies may also be used to localize cytotoxic agents to cells which express Ly6E. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Ly6E as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof.

Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Ly6E antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-Ly6E antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Ly6E antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frupperda cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Ly6E antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to Ly6E. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized Ly6E is incubated in a solution comprising a first labeled antibody that binds to Ly6E (e.g., any of the antibodies described herein) and a second unlabeled antibody that is being tested for its ability to compete with the first antibody for binding to Ly6E. The second antibody may be present in a hybridoma supernatant. As a control, immobilized Ly6E is incubated in a solution comprising the first labeled antibody but not the second unlabeled antibody. After incubation under conditions permissive for binding of the first antibody to Ly6E, excess unbound antibody is removed, and the amount of label associated with immobilized Ly6E is measured. If the amount of label associated with immobilized Ly6E is substantially reduced in the test sample relative to the control sample, then that indicates that the second antibody is competing with the first antibody for binding to Ly6E. See Harlow and Lane (1988) *Antibodies: A Laboratory Manual* ch.14 (Cold Spring Harbor Laboratory, Cold Spring Harbor, N.Y.).

D. Immunoconjugates

The invention also provides immunoconjugates comprising an anti-Ly6E antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chan, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity.

E. Methods and Compositions for Diagnostics and Detection

In certain embodiments, any of the anti-Ly6E antibodies provided herein is useful for detecting the presence of Ly6E in a biological sample. The term "detecting" as used herein encompasses quantitative or qualitative detection. A "biological sample" comprises, e.g., a cell or tissue (e.g., biopsy material, including cancerous or potentially cancerous colon, colorectal, endometrial, pancreatic, or ovarian tissue).

In one embodiment, an anti-Ly6E antibody for use in a method of diagnosis or detection is provided. In a further aspect, a method of detecting the presence of Ly6E in a biological sample is provided. In certain embodiments, the method comprises contacting the biological sample with an anti-Ly6E antibody as described herein under conditions permissive for binding of the anti-Ly6E antibody to Ly6E, and detecting whether a complex is formed between the anti-Ly6E antibody and Ly6E in the biological sample. Such method may be an in vitro or in vivo method. In one embodiment, an anti-Ly6E antibody is used to select subjects eligible for therapy with an anti-Ly6E antibody, e.g. where Ly6E is a biomarker for selection of patients. In a further embodiment, the biological sample is a cell or tissue (e.g., biopsy material, including cancerous or potentially cancerous colon, colorectal, endometrial, pancreatic, or ovarian tissue).

In a further embodiment, an anti-Ly6E antibody is used in vivo to detect, e.g., by in vivo imaging, A Ly6E-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., The Oncologist 12:1379-1389 (2007) and Verel et al., *J. Nucl. Med.* 44:1271-1281 (2003). In such embodiments, a method is provided for detecting A Ly6E-positive cancer in a subject, the method comprising administering a labeled anti-Ly6E antibody to a subject having or suspected of having A Ly6E-positive cancer, and detecting the labeled anti-Ly6E antibody in the subject, wherein detection of the labeled anti-Ly6E antibody indicates A Ly6E-positive cancer in the subject. In certain of such embodiments, the labeled anti-Ly6E antibody comprises an anti-Ly6E antibody conjugated to a positron emitter, such as $^{68}$Ga, $^{18}$F, $^{64}$Cu, $^{86}$Y, $^{76}$Br, $^{89}$Zr, and $^{124}$I. In a particular embodiment, the positron emitter is $^{89}$Zr. Nonlimiting exemplary methods of making and using $^{89}$Zr-labeled antibodies are described, e.g., in PCT Publication No. WO 2011/056983. In some embodiments, the labeled anti-Ly6E antibody is a cysteine engineered antibody conjugated to one or more zirconium complexes. See, e.g., WO 2011/056983.

In further embodiments, a method of diagnosis or detection comprises contacting a first anti-Ly6E antibody immobilized to a substrate with a biological sample to be tested for the presence of Ly6E, exposing the substrate to a second anti-Ly6E antibody, and detecting whether the second anti-Ly6E is bound to a complex between the first anti-Ly6E antibody and Ly6E in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colorectal, endometrial, pancreatic or ovarian tissue). In certain embodiments, the first or second anti-Ly6E antibody is any of the antibodies described herein. In such embodiments, the second anti-Ly6E antibody may be 6D3 or 7C9; or antibodies derived from 6D3 or 7C9 as described herein.

Exemplary disorders that may be diagnosed or detected according to any of the above embodiments include Ly6E-positive cancers, such as Ly6E-positive breast cancer (including Her2 positive breast cancer, Her2 negative breast cancer, Her2 negative/hormone receptor positive (Her2−/ER+/PR+) breast cancer, triple negative (Her2−/ER−/PR−) breast cancer), Ly6E-positive colon cancer, Ly6E-positive colorectal cancer (including adenocarcinoma), Ly6E-positive melanoma, Ly6E-positive ovarian cancer (including ovarian serous adenocarcinoma), Ly6E-positive pancreatic cancer (including pancreatic ductal adenocarcinoma), Ly6E-positive lung cancer, Ly6E-positive non-small cell lung cancer (e.g., squamous or non-squamous, such as adenocarcinoma), Ly6E-positive gastric cancer, Ly6E-positive esophageal cancer, Ly6E-positive head and neck cancer, Ly6E-positive kidney cancer, Ly6E-positive soft tissue cancer, Ly6E-positive melanoma, and Ly6E-positive endometrial cancer. In some embodiments, A Ly6E-positive cancer is a cancer that receives an anti-Ly6E immunohistochemistry (IHC) or in situ hybridization (ISH) score greater than "0," which corresponds to very weak or no staining in >90% of tumor cells. In some embodiments, a Ly6E-positive cancer expresses Ly6E at a 1+, 2+ or 3+ level, as defined under the conditions described herein in Example 4. In some embodiments, 1+, 2+, and 3+ immunohistochemistry staining is determined according to Table 3. In some embodiments, A Ly6E-positive cancer is a cancer that expresses Ly6E according to a reverse-transcriptase PCR (RT-PCR) assay that detects Ly6E mRNA. In some embodiments, the RT-PCR is quantitative RT-PCR.

In certain embodiments, labeled anti-Ly6E antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-Ly6E antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, in some instances, it may be desirable to further provide a platinum complex, e.g., for the treatment of Ly6E-positive cancer such as, for example, a Ly6E-positive breast cancer (including Her2 positive breast cancer, Her2 negative breast cancer, Her2 negative/hormone receptor positive (Her2-/ER+/PR+) breast cancer, triple negative (Her2-/ER-/PR-) breast cancer), or a Ly6E-positive pancreatic cancer, or a Ly6E-positive colon cancer, or a Ly6E-positive colorectal cancer, or a Ly6E-positive melanoma, or a Ly6E-positive ovarian cancer, or a Ly6E-positive non-small cell lung cancer (e.g., squamous or non-squamous, such as adenocarcinoma), or a Ly6E-positive gastric cancer, or a Ly6E-positive esophageal cancer, or a Ly6E-positive head and neck cancer, or a Ly6E-positive kidney cancer, or a Ly6E-positive soft tissue cancer, or a Ly6E-positive endometrial cancer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Ly6E antibodies or immunoconjugates provided herein may be used in methods, e.g., therapeutic methods.

In one aspect, an anti-Ly6E antibody or immunoconjugate provided herein is used in a method of inhibiting proliferation of a Ly6E-positive cell, the method comprising exposing the cell to the anti-Ly6E antibody or immunoconjugate under conditions permissive for binding of the anti-Ly6E antibody or immunoconjugate to Ly6E on the surface of the cell, thereby inhibiting the proliferation of the cell. In certain embodiments, the method is an in vitro or an in vivo method. In further embodiments, the cell is a breast cancer cell (including Her2 positive breast cancer cell, Her2 negative breast cancer cell, Her2 negative/hormone receptor positive (Her2-/ER+/PR+) breast cancer cell, triple negative (Her2-/ER-/PR-) breast cancer cell), or a pancreatic cancer cell, or a colon cancer cell, or a colorectal cancer cell, or a melanoma cancer cell, or an ovarian cancer cell, or a non-small cell lung cancer cell (e.g., squamous or non-squamous, such as adenocarcinoma), a gastric cancer cell, or an esophageal cancer, or a head and neck cancer, or a kidney cancer, or a soft tissue cancer, or an endometrial cancer cell.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-Ly6E antibody or immunoconjugate for use as a medicament is provided. In further aspects, an anti-Ly6E antibody or immunoconjugate for use in a method of treatment is provided. In certain embodiments, an anti-Ly6E antibody or immunoconjugate for use in treating Ly6E-positive cancer is provided. In certain embodiments, the invention provides an anti-Ly6E antibody or immunoconjugate for use in a method of treating an individual having a Ly6E-positive cancer, the method comprising administering to the individual an effective amount of the anti-Ly6E antibody or immunoconjugate. In one such embodiment, the method further comprises administering to the individual an effective amount of at least one additional therapeutic agent, e.g., as described below.

In a further aspect, the invention provides for the use of an anti-Ly6E antibody or immunoconjugate in the manufacture or preparation of a medicament. In one embodiment, the medicament is for treatment of Ly6E-positive cancer. In a further embodiment, the medicament is for use in a method of treating Ly6E-positive cancer, the method comprising administering to an individual having Ly6E-positive cancer an effective amount of the medicament. In one such embodiment, the method further comprises administering to the individual an effective amount of at least one additional therapeutic agent, e.g., as described below.

In a further aspect, the invention provides a method for treating Ly6E-positive cancer. In one embodiment, the method comprises administering to an individual having such Ly6E-positive cancer an effective amount of an anti-Ly6E antibody or immunoconjugate. In one such embodiment, the method further comprises administering to the individual an effective amount of at least one additional therapeutic agent, as described below.

A Ly6E-positive cancer according to any of the above embodiments may be, e.g., Ly6E-positive breast cancer (including Her2 positive breast cancer, Her2 negative breast cancer, Her2 negative/hormone receptor positive (Her2-/ER+/PR+) breast cancer, triple negative (Her2-/ER-/PR-) breast cancer), Ly6E-positive colon cancer, Ly6E-positive colorectal cancer (including adenocarcinoma), Ly6E-positive melanoma, Ly6E-positive ovarian cancer (including ovarian serous adenocarcinoma), Ly6E-positive pancreatic cancer (including pancreatic ductal adenocarcinoma), Ly6E-positive lung cancer, Ly6E-positive non-small cell lung cancer (e.g., squamous or non-squamous, such as adenocarcinoma), Ly6E-positive gastric cancer, Ly6E-positive esophageal cancer, Ly6E-positive head and neck cancer, Ly6E-positive kidney cancer, Ly6E-positive soft tissue cancer, Ly6E-positive melanoma, and Ly6E-positive endometrial cancer. In some embodiments, a Ly6E-positive cancer is a cancer that receives an anti-Ly6E immunohistochemistry (IHC) or in situ hybridization (ISH) score greater than "0," which corresponds to very weak or no staining in >90% of tumor cells, under the conditions described herein. In another embodiment, a Ly6E-positive cancer expresses Ly6E at a 1+, 2+ or 3+ level, as defined under the conditions described herein. In some embodiments, a Ly6E-positive cancer is a cancer that expresses Ly6E according to a reverse-transcriptase PCR (RT-PCR) assay that detects Ly6E mRNA. In some embodiments, the RT-PCR is quantitative RT-PCR.

An "individual" according to any of the above embodiments may be a human.

In a further aspect, the invention provides pharmaceutical formulations comprising any of the anti-Ly6E antibodies or immunoconjugate provided herein, e.g., for use in any of the above therapeutic methods. In one embodiment, a pharmaceutical formulation comprises any of the anti-Ly6E antibodies or immunoconjugates provided herein and a pharmaceutically acceptable carrier. In another embodiment, a pharmaceutical formulation comprises any of the anti-Ly6E antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is a platinum complex, e.g., for the treatment of Ly6E-positive cancer such as, for example, a Ly6E-positive breast cancer (including Her2 positive breast cancer, Her2 negative breast cancer, Her2 negative/hormone receptor positive (Her2−/ER+/PR+) breast cancer, triple negative (Her2−/ER−/PR−) breast cancer), Ly6E-positive colon cancer, Ly6E-positive colorectal cancer (including adenocarcinoma), Ly6E-positive melanoma, Ly6E-positive ovarian cancer (including ovarian serous adenocarcinoma), Ly6E-positive pancreatic cancer (including pancreatic ductal adenocarcinoma), Ly6E-positive lung cancer, Ly6E-positive non-small cell lung cancer (e.g., squamous or non-squamous, such as adenocarcinoma), Ly6E-positive gastric cancer, Ly6E-positive esophageal cancer, Ly6E-positive head and neck cancer, Ly6E-positive kidney cancer, Ly6E-positive soft tissue cancer, Ly6E-positive melanoma, and Ly6E-positive endometrial cancer.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 μg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-Ly6E antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

I. Sequences of the Invention

In another aspect of the invention, the following sequences useful for the treatment, prevention and/or diagnosis of the disorders described above are provided.

| SEQ ID NO: | SEQUENCE | DESCRIPTION |
|---|---|---|
| 1 | MKIFLPVLLAALLGVERASSLMCFSCLNQKSN LYCLKPTICSDQDNYCVTVSASAGIGNLVTFG HSLSKTCSPACPIPEGVNVGVASMGISCCQSF LCNFSAADGGLRASVTLLGAGLLLSLLPALLR FGP | HUMAN Ly6E amino acid sequence with signal sequence (amino acids 1-20, underlined) |
| 2 | MKIFLPVLLAALLGVERASSLMCFSCLNQKSN LYCLKPTICSDQDNYCVTVSTSAGIGNLVTFG HSLSKTCSPACPLPEGINVGVASMGISCCQSF LCNFSAADGGLRASATLLGAGLLLSLLPALLR FGP | CYNOMOLOGOUS Ly6E amino acid sequence with signal sequence (amino acids 1-20, underlined) |
| 3 | DIQMTQSPSSLSASVGDRVTITCSASQGISNY LNWYQQKPGKTVKLLIYYTSNLHSGVPSRFSG SGSGTDYTLTISSLQPEDFATYYCQQYSELPW TFGQGTKVEIK | Humanized variable light chain amino acid sequence of anti-Ly6E antibody clone hu9B12 v12 |
| 4 | DIQMTQTTSSLSASLGDRVTISCSASQGISNY LNWYQQKPDGTVKLLIYYTSNLHSGVPSRFSG SGSGTDYSLTISNLEPEDIATYYCQQYSELPW TFGGGTKVEIK | Chimeric variable light chain amino acid sequence of anti-Ly6E antibody clone xLy6E mu9B12 |
| 5 | EVQLVESGPALVKPTQTLTLTCTVSGFSLTGY SVNWIRQPPGKALEWLGMIWGDGSTDYNSALK SRLTISKDTSKNQVVLTMTNMDPVDTATYYCA RDYYFNYASWFAYWGQGTLVTVSS | Humanized variable heavy chain amino acid sequence of anti-Ly6E antibody clone hu9B12 v12 |
| 6 | QVQLKESGPGLVAPSQSLSLTCTVSGFSLTGY SVNWVRQPPGKGLEWLGMIWGDGSTDYNSALK SRLTISKDNSKSQVFLKMNSLQTDDTARYYCA RDYYFNYASWFAYWGPGTLVTVSA | Chimeric variable heavy chain amino acid sequence of anti-Ly6E antibody clone xLy6E mu9B12 |
| 7 | SASQGISNYLN | hu9B12 v12 hypervariable region (HVR)-L1 |
| 8 | YTSNLHS | hu9B12 v12 HVR-L2 |
| 9 | QQYSELPWT | hu9B12 v12 HVR-L3 |
| 10 | GFSLTGYSVN | hu9B12 v12 HVR-H1 |
| 11 | MIWGDGSTDYNSALKS | hu9B12 v12 HVR-H2 |
| 12 | DYYVNYASWFAY | hu9B12 v12 HVR-H3 |
| 19 | DIQMTQSPSSLSASVGDRVTITC | hu9B12 v12 light chain (LC) framework region (FR) 1 |
| 20 | WYQQKPGKTVKLLIY | hu9B12 v12 LC FR2 |
| 21 | GVPSRFSGSGSGTDYTLTISSLQPEDFATYYC | hu9B12 v12 LC FR3 |
| 22 | FGQGTKVEIK | hu9B12 v12 LC FR4 |
| 23 | EVQLVESGPALVKPTQTLTLTCTVS | hu9B12 v12 HC FR1 |
| 24 | WIRQPPGKALEWLG | hu9B12 v12 HC FR2 |
| 25 | RLTISKDTSKNQVVLTMTNMDPVDTATYYCAR | hu9B12 v12 HC FR3 |
| 26 | WGQGTLVTVSS | hu9B12 v12 HC FR4 |

| SEQ ID NO: | SEQUENCE | DESCRIPTION |
|---|---|---|
| 27 | DPVVTQTPSS ASAAVGGTVS ISCQSSQSVY NNNYLGWYQQ KPGQPPKLLI YDASKLASGV PSRFKASGSG TQFALTISDL ECDDAATYYC VGGYPGSLNV FGGGTEVVVK | Rabbit variable light chain amino acid sequence of anti-Ly6E antibody clone GEN-93-8-1 |
| 28 | QSVEESGGRL VTPGTPLTLT CATSGFSLSI YDMTWVRQAP GKGLEWIGVI YTSGGAYYAN WAKGRFTISR TSTTVDLRMT SPTTEDTATY FCVRNWAHGS DLWGQGTLVT VSS | Rabbit variable heavy chain amino acid sequence of anti-Ly6E antibody clone GEN-93-8-1 |
| 29 | QSSQSVYNNNYLG | GEN-93-8-1 hypervariable region (HVR)-L1 |
| 30 | DASKLAS | GEN-93-8-1 HVR-L2 |
| 31 | VGGYPGSLNV | GEN-93-8-1 HVR-L3 |
| 32 | IYDMT | GEN-93-8-1 HVR-H1 |
| 33 | VIYTSGGAYYANWA | GEN-93-8-1 HVR-H2 |
| 34 | NWAHGSDL | GEN-93-8-1 HVR-H3 |
| 35 | MKIFLPVLLAALLGVERASSLMCFSCLNQKSN LYCLKPTICSDQDNYCVTVSTSAGIGNLVTFG HSLSKTCSPACPLPEGINVGVASMGISCCQSF LCNFSAADGGLRASATLLGAGLLLSLLPALLR FGP | RHESUS Ly6E amino acid sequence with signal sequence (amino acids 1-20, underlined) |
| 36 | MSATSNMRVFLPVLLAALLGMEQVHSLMCFSC TDQKNNINCLWPVSCQEKDHYCITLSAAAGFG NVNLGYTLNKGCSPICPSENVNLNLGVASVNS YCCQSSFCNFSAAGLGLRASIPLLGLGLLLSL LALLQLSP | MOUSE Ly6E amino acid sequence with signal sequence (amino acids 1-26, underlined) |
| 37 | MSAASSMRVFLPVLLAALLGVEQVHSLMCFSC TDQKNNINCLWPVSCSSTDNYCITLSAAAGFG NVNLGYTLNKGCSPTCPRENININLGVASVNS YCCQSSFCNFSTAGLGLRASIPLLGLGLLLSL LAVLRLSP | RAT Ly6E amino acid sequence with signal sequence (amino acids 1-26, underlined) |
| 38 | LMCFSCLNQKSNLYCLKPTICSDQDNYCVTVS ASAGIGNLVTFGHSLSKTCSPACPIPEGVNVG VASMGISCCQSFLCNFSAADGGLRASVTLLGA GLLLSLLPALLRFGP | Mature HUMAN Ly6E amino acid sequence (without signal sequence) |
| 39 | LMCFSCLNQKSNLYCLKPTICSDQDNYCVTVS TSAGIGNLVTFGHSLSKTCSPACPLPEGINVG VASMGISCCQSFLCNFSAADGGLRASATLLGA GLLLSLLPALLRFGP | Mature CYNOMOLOGOUS Ly6E amino acid sequence (without signal sequence) |
| 40 | LMCFSCLNQKSNLYCLKPTICSDQDNYCVTVS TSAGIGNLVTFGHSLSKTCSPACPLPEGINVG VASMGISCCQSFLCNFSAADGGLRASATLLGA GLLLSLLPALLRFGP | Mature RHESUS Ly6E amino acid sequence (without signal sequence) |
| 41 | LMCFSCTDQKNNINCLWPVSCQEKDHYCITLS AAAGFGNVNLGYTLNKGCSPICPSENVNLNLG VASVNSYCCQSSFCNFSAAGLGLRASIPLLGL GLLLSLLALLQLSP | Mature MOUSE Ly6E amino acid sequence (without signal sequence) |
| 42 | LMCFSCTDQKNNINCLWPVSCSSTDNYCITLS AAAGFGNVNLGYTLNKGCSPTCPRENININLG VASVNSYCCQSSFCNFSTAGLGLRASIPLLGL GLLLSLLAVLRLSP | Mature RAT Ly6E amino acid sequence (without signal sequence) |
| 43 | EVQLVESGGGLVQPGGSLRLSCAASGFSLTGY SVNWVRQAPGKGLEWVGMIWDGSTDYNSALK SRFTISRDNSKNTLYLQMNSLRAEDTAVYYCA RDYYFNYASWFAYWGQGTLVTVSS | Humanized variable heavy chain amino acid sequence of hu9B12 VH3 graft |

| SEQ ID NO: | SEQUENCE | DESCRIPTION |
|---|---|---|
| 44 | QVQLKESGPGLVAPSQSLSLTCTVSGFSLTGY SVNWVRQPPGKGLEWLGMIWGDGSTDYNSALK SRLTISKDNSKSQVFLKMNSLQTDDTARYYCA RDYYFNYASWFAYWGPGTLVTVSA | Chimeric variable heavy chain amino acid sequence of xLy6E mu9B12 in VH3 graft |

III. Examples

The following are examples of methods and compositions of the invention. It is understood that various other embodiments may be practiced, given the general description provided above.

Example 1

Human Ly6E Gene Expression

GeneLogic Profile: For the analysis of Ly6E mRNA expression in multiple human tumor and normal biopsy samples, the Affymetrix data were obtained from Gene Logic Inc. The analysis shown for probe set ID 202145_at was carried out using the HGU133 Plus v2 GENECHIP® on 3,879 normal human tissue samples (green symbols), 1,605 human cancer tissue samples (red symbols: 1,291 primary and 314 metastatic), and 3,872 human noncancer disease tissue samples (blue symbols). Microarray data were normalized using the Affymetrix MAS (Microarray Analysis Suite) version 5.0 software, with sample expression values scaled to a trimmed mean of 500.

This analysis showed that Ly6E was specifically overexpressed in breast, pancreatic, colon, lung and ovarian cancers, among others, with low/no detection of Ly6E in normal tissues (FIG. 2).

In Situ Hybridization (ISH): In situ hybridization was performed on ovarian cancer tissue microarray (TMA) for evaluating prevalence of Ly6E per methods established in Methods Mol Biol, 2006; 326:255-64.

```
Forward primer
                         SEQ ID NO: 45
GTG CCT GAT CTG TGC CCT TGG- Reverse primer
                         SEQ ID NO: 46
CCC GGA AGT GGC AGA AAC CC-
```

Probe sequence:

```
                                          SEQ ID NO: 47
GTGCCTGATCTGTGCCCTTGGTCCCAGGTCAGGCCCACCCCCTGCACC

TCCACCTGCCCCAGCCCCTGCCTCTGCCCAAGTGGGCCAGCTGCCCTC

ACTTCTGGGGTGGATGATGTGACCTTCCTTGGGGGACTGCGGAAGGGA

CGAGGGTTCCCTGGAGTCTTACGGTCCAACATCAGACCAAGTCCCATG

GACATGCTGACAGGGTCCCCAGGGAGACCGTGTCAGTAGGGATGTGTG

CCTGGCTGTGTACGTGGGTGTGCAGTGCACGTGAGAGCACGTGGCGGC

TTCTGGGGGCCATGTTTGGGGAGGGAGGTGTGCCAGCAGCCTGGAGAG

CCTCAGTCCCTGTAGCCCCCTGCCCTGGCACAGCTGCATGCACTTCAA

GGGCAGCCTTTGGGGGTTGGGGTTTCTGCCACTTCCGGG-.
```

The results indicated that 47/65 (72%) of ovarian tumors analyzed showed Ly6E expression (data not shown).

Immunohistochemistry (IHC): Immunohistochemistry was performed on 4 μm thick formalin-fixed paraffin embedded (FFPE) tissue sections mounted on glass slides. Slides were deparaffinized in xylene and rehydrated through graded alcohols to distilled water. Slides were pretreated with Target Retrieval solution (Dako, Carpinteria, Calif., USA) for 20 minutes at 99° C. Slides were then treated with KPL blocking solution (Kierkegaard and Perry Laboratories, Gaithersburg, Md., USA) and avidin/biotin block (Vector Laboratories, Burlingame, Calif., USA) respectively. Non-specific IgG binding was blocked with 10% horse serum (Life Technologies, Carlsbad, Calif., USA) in 3% bovine serum albumin (Roche, Basel, Switzerland) in phosphate buffered saline. Primary antibody, mouse anti-Ly6E, clone 10G7.7.8 was diluted 10 μg/mL and incubated on slides for 60 minutes at room temperature.

Slides were rinsed, incubated with horse anti-mouse IgG biotinylated secondary (Vector Labs) followed by incubation in Vectastain ABC Elite reagent (Vector Labs). Slides were then incubated in Pierce metal enhanced DAB (Thermo Scientific; Fremont, Calif.), counterstained, dehydrated and coverslipped.

From IHC studies using mouse anti-Ly6E clone 10G7.7.8, the prevalence of Ly6E was detected at 27-36% in breast cancer, ~40% in pancreatic cancer, ~26% in colon cancer, 17-26% in melanoma, ~29% in NSCLC (data not shown).

Immunohistochemistry on Normal Tissues Using Mouse Anti-Ly6E Clone 10G7.7.8: On a panel of normal human and cynomolgus monkey tissues, low and moderate Ly6E expression is detected in the stomach and salivary glands of both human and cynomolgus monkey, low to moderate Ly6E expression is detected in a subpopulation of cells in the adrenal cortex in cynomolgus monkey and to a lesser extent in human specimens and moderate expression of Ly6E is detected in the transitional epithelium of the urinary bladder (only cynomolgus monkey was examined). Table 2 below tabulates immunohistochemical (IHC) expression of Ly6E determined using mouse anti-Ly6E clone 10G7.7.8 in a comprehensive human and cynomolgus monkey normal tissue panel. Low (LOW) to moderate (MOD) Ly6E expression is limited to highlighted tissues in grey (adrenal cortex, cervix, salivary glands, stomach and urinary bladder). ND=not done. NO=no expression.

TABLE 2

| Normal Tissue | Human | Cyno |
|---|---|---|
| Abdominal Cavity | ND | NO |
| Adrenal | LOW (⅓) | MOD |
| Bone Marrow | NO | NO |
| Brain | NO | NO |
| Breast | NO | NO |
| Cervix | MOD (⅓) | NO |
| Colon | NO | NO |
| Esophagus | NO | NO |
| Eye | NO | NO |
| Heart | NO | NO |
| Intestine Small | NO | NO |
| Kidney | NO | NO |
| Larynx | NO | NO |
| Liver | NO | NO |
| Lung | NO | NO |
| Pancreas | NO | NO |
| Parathyroid | NO | ND |
| Pituitary | ND | NO |
| Prostate | NO | NO |
| Salivary Gland | MOD | MOD |
| Skeletal Muscle | NO | NO |
| Skin | NO | NO |
| Spleen | NO | NO |
| Stomach | LOW | LOW |
| Testis | NO | NO |
| Thymus | NO | NO |
| Thyroid | NO | NO |
| Tonsil | NO | NO |
| Urinary Bladder | ND | MOD |
| Uterus | NO | NO |

Example 2

Quantitative PCR (QRT PCR)

Human major tissue qPCR Array containing 1st strand DNA from a panel of 48 normal tissues from Origene, Rockville, Md. (HMRT 102) was assayed for Ly6E RNA expression. Ly6E expression in a panel of select cancer cell lines and tissues (breast and pancreatic) were assayed in parallel. Taqman assays were set up using reagents, instrumentation and software from Applied Biosystems (ABI, Foster City, Calif.). Primer-probe sets were designed with primers flanking a fluorogenic probe dual labeled with Reporter dye FAM and quencher dye TAMRA.

Primer-probe set for RPL19:

```
Forward primer-
                            (SEQ ID NO: 48)
5' AGC GGA TTC TCA TGG AAC A;

Reverse primer-
                            (SEQ ID NO: 49)
5' CTG GTC AGC CAG GAG CTT
and probe-
                            (SEQ ID NO: 50)
5' TCC ACA AGC TGA AGG CAG ACA AGG.
```

Primer-probe set for Ly6E:

```
Forward primer-
                            (SEQ ID NO: 51)
5' AGA AGG CGT CAA TGT TGG T;

Reverse primer-
                            (SEQ ID NO: 52)
5' CAC TGA AAT TGC ACA GAA AGC
and probe-
                            (SEQ ID NO: 53)
5' TTC CAT GGG CAT CAG CTG CTG.
```

Figure 3:
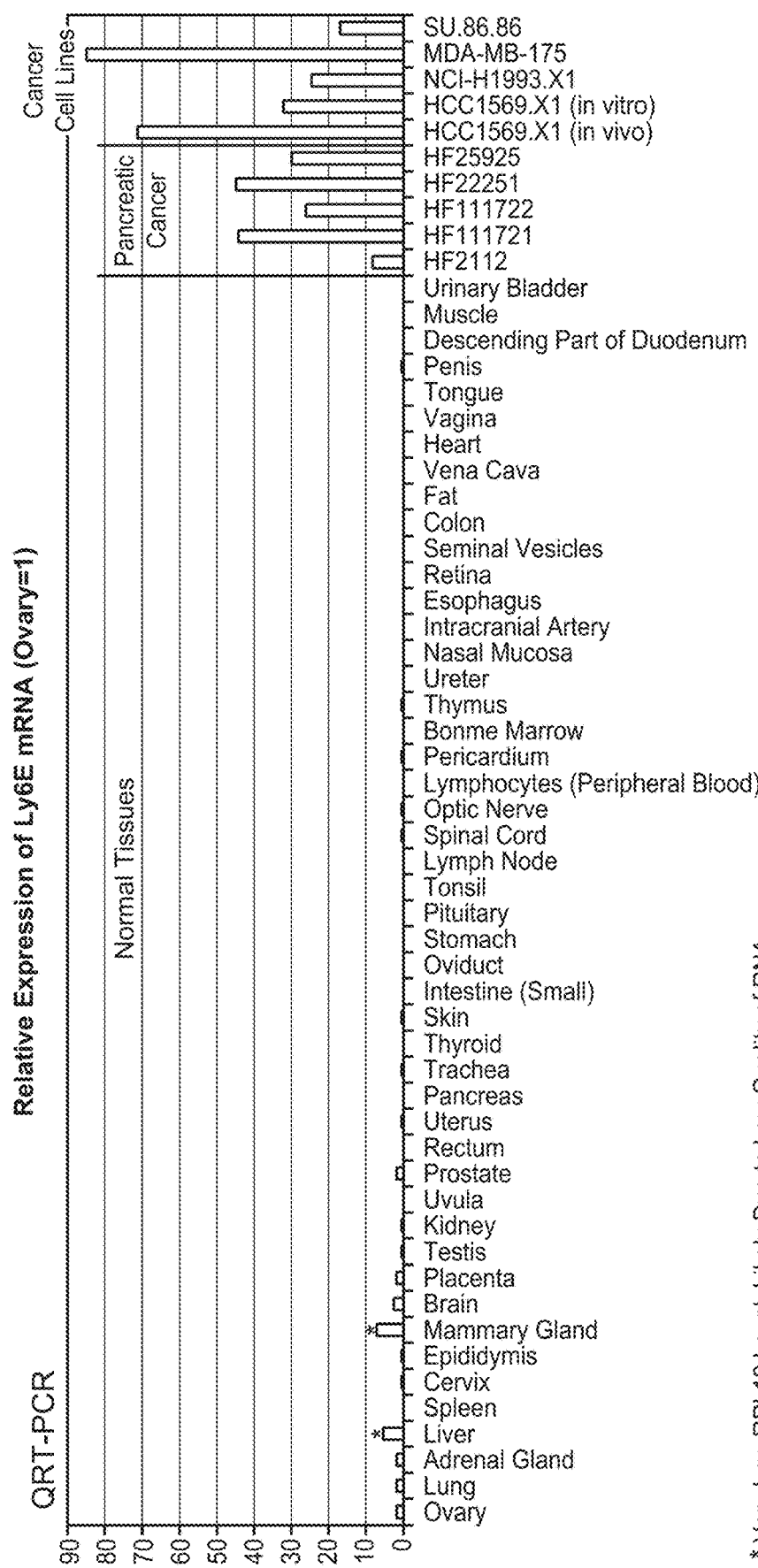
FIG. 3 a depicts QRT-PCR relative fold change in Ly6E transcript expression normalized to expression of RPL19 control gene in a panel of normal human tissues and select cancer cell lines and tissues as described in Example 2. The results indicate that the Ly6E transcript expression in normal tissues is low compared to expression of Ly6E in breast and pancreatic cancers.
Figure 5A:
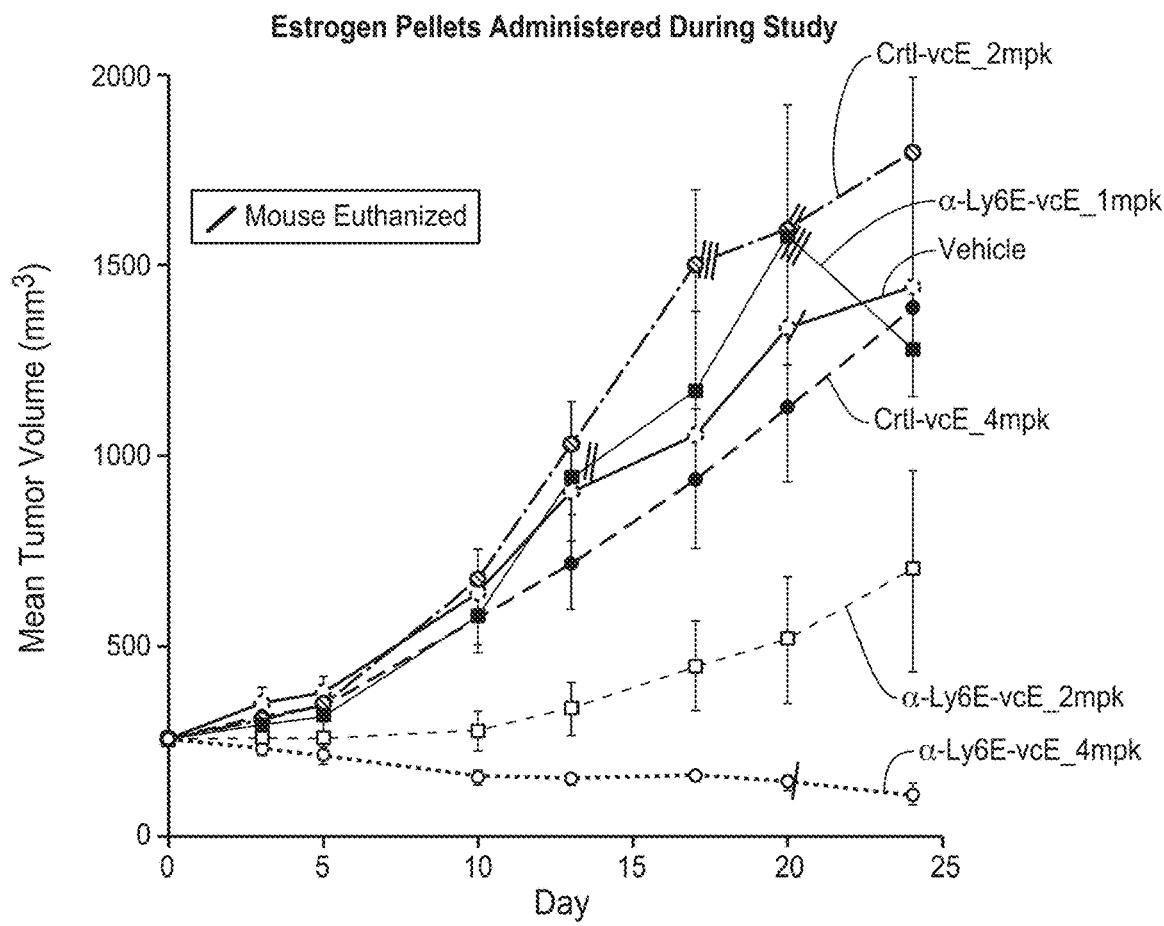
FIGS. 5A-E show the in vivo efficacy of an anti-Ly6E ADC in an epidermal growth factor receptor, Her2 amplified breast cancer xenograft mouse model as described in Example 7. Panel A shows subcutaneous tumors established in immunodeficient mice inoculated with HCC1569 X2 breast cancer cells. When tumor volumes reached approximately 100-250 mm$^3$ (day 0), animals were given a single IV injection of either control ADC (Control-vc-MMAE) or a humanized anti-Ly6E (hu9B12 v12) ADC (MC-vc-PAB-MMAE) at the indicated doses. Average tumor volumes with standard deviations were determined from 9 animals per groups (indicated on graph). Panel B shows surface Ly6E protein expression in live HCC1569 X2 cells as seen by flow cytometry, where the gray peak indicates cells treated to secondary detection reagent alone and the black peak indicates cells treated with 3 µg/mL Ly6E antibody (hu9B12 v12) ADC followed by treatment with ALEXA FLUOR® 488 conjugated to Human IgG as a secondary detection reagent. Expression of Ly6E as a GeoMean value is shown to the right of the histogram. Panel C shows cell killing by hu9B12 v12 ADC titration for the breast cancer cell line HCC1569 X2. The indicated concentrations of hu9B12 v12 ADC, control IgG-vc-MMAE, or equivalent amount of PBS vehicle control were incubated with cells for 5 days and relative cell viability (y-axis) assessed using CELLTITER-GLO®. Panel D shows 1+/2+Ly6E staining on HCC1569 X2 tumor by immunohistochemistry using mouse anti-Ly6E clone 10G7.7.8. The percent of tumor cells staining at a 1+ level for Ly6E using mouse anti-Ly6E clone 10G7.7.8 is indicated. Panel E shows 3+ Ly6E staining on HCC1569 X2 cell pellet by immunohistochemistry using rabbit anti-Ly6E antibody clone GEN-93-8-1.
Figure 5B:
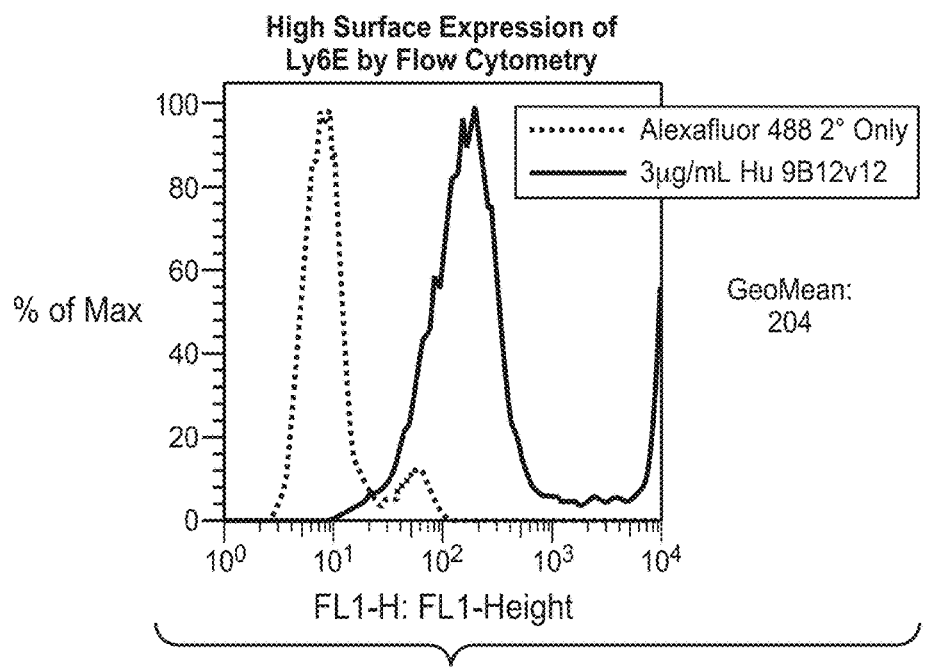
Figure 5C:
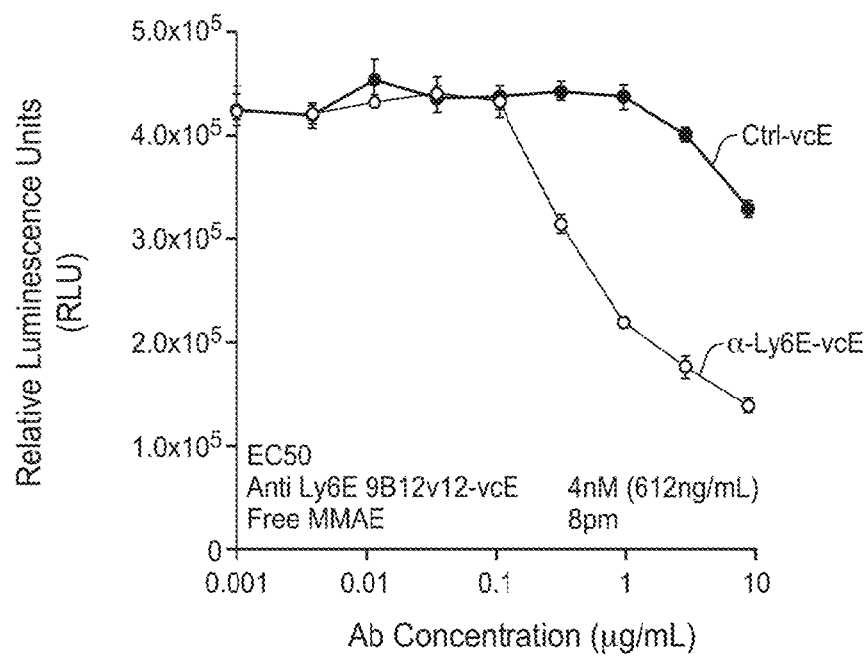
Figure 5D:
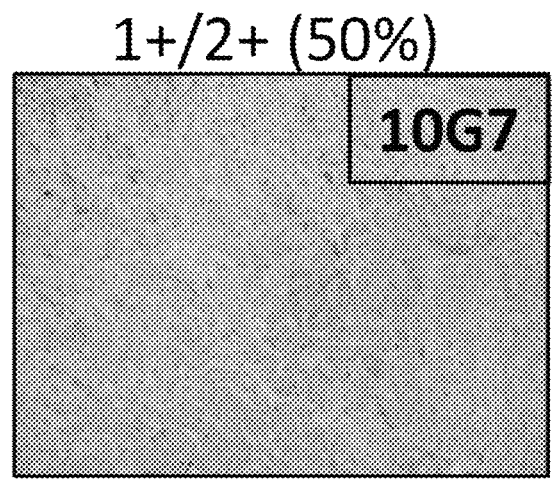
Figure 5E:
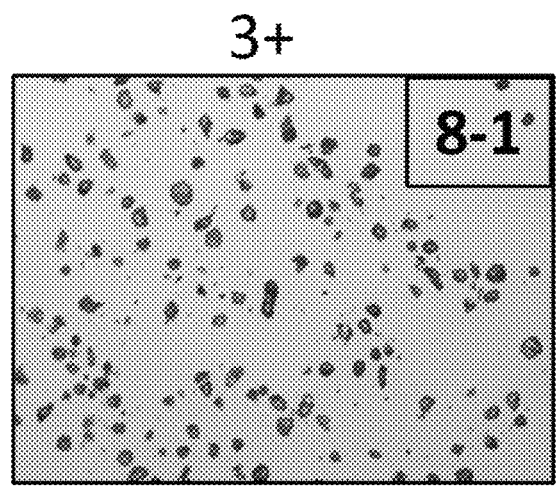
Figure 6A:
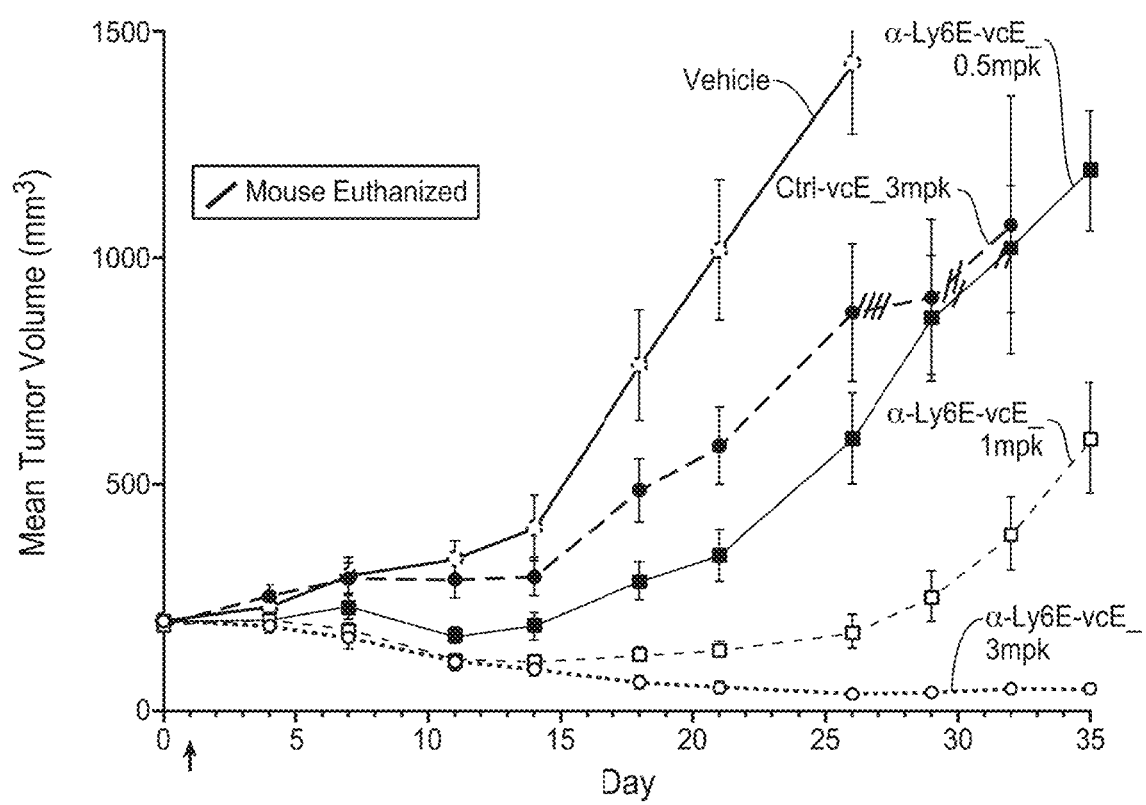
FIGS. 6A-E show the in vivo efficacy of an anti-Ly6E ADC in a pancreatic cancer xenograft mouse model. Panel A shows subcutaneous tumors established in immunodeficient mice inoculated with SU.86.86 pancreatic cancer cells. When tumor volumes reached approximately 100-250 mm$^3$ (day 0), animals were given a single IV injection of either control ADC (Control-vc-MMAE) or anti-Ly6E ADC, as described in FIG. 5, at the indicated doses. Average tumor volumes with standard deviations were determined from 9 animals per groups (indicated on graph). Panel B compares total Ly6E protein expression in HCC1569 X2 and SU.86.86 cell lysates by immunoblotting using rabbit anti-Ly6E antibody clone GEN-93-8-1. Total β-tubulin protein levels were measured in parallel to serve as loading controls. Panel C shows shows 1+Ly6E staining on SU.86.86 tumor by immunohistochemistry using mouse anti-Ly6E clone 10G7.7.8. Panel D cell killing by anti-Ly6E ADC titration for the pancreatic cancer cell line SU.86.86. The indicated concentrations of anti-Ly6E ADC, control IgG-vc-MMAE, or equivalent amount of PBS vehicle control were incubated with cells for 5 days and relative cell viability in relative luminescence units (RLU) (y-axis) was assessed using CELLTITER-GLO®. Panel E shows 2+ Ly6E staining on SU.86.86 tumor by immunohistochemistry using rabbit anti-Ly6E antibody clone GEN-93-8-1.
Figure 6B:
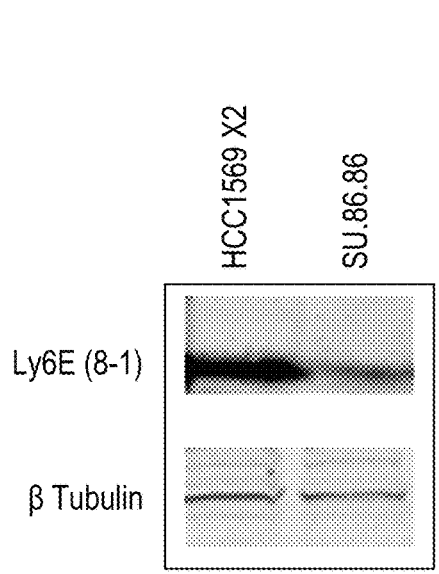
Figure 6C:
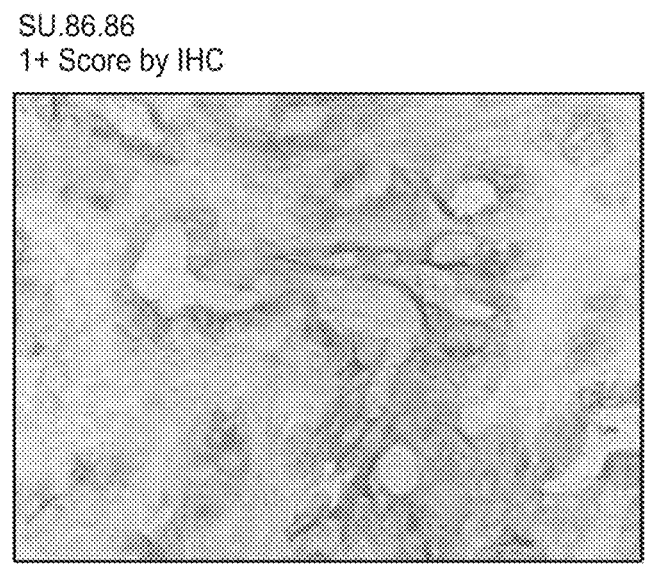
Figure 6D:
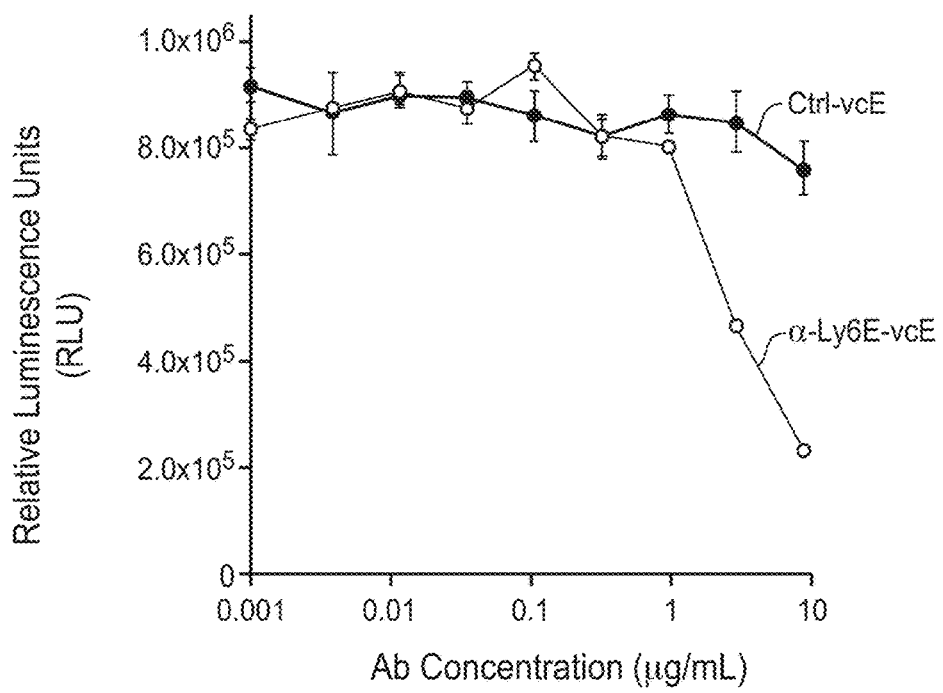
Figure 6E:
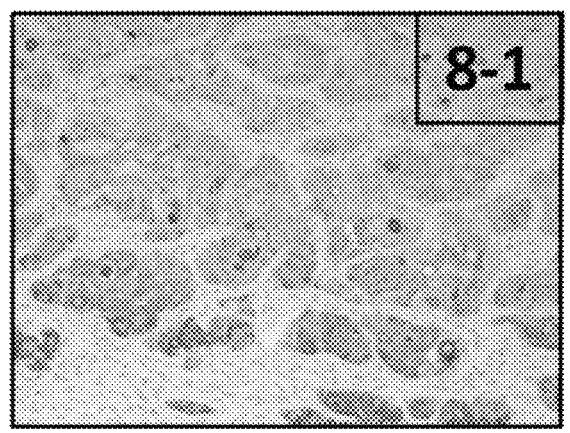
Figure 7A:
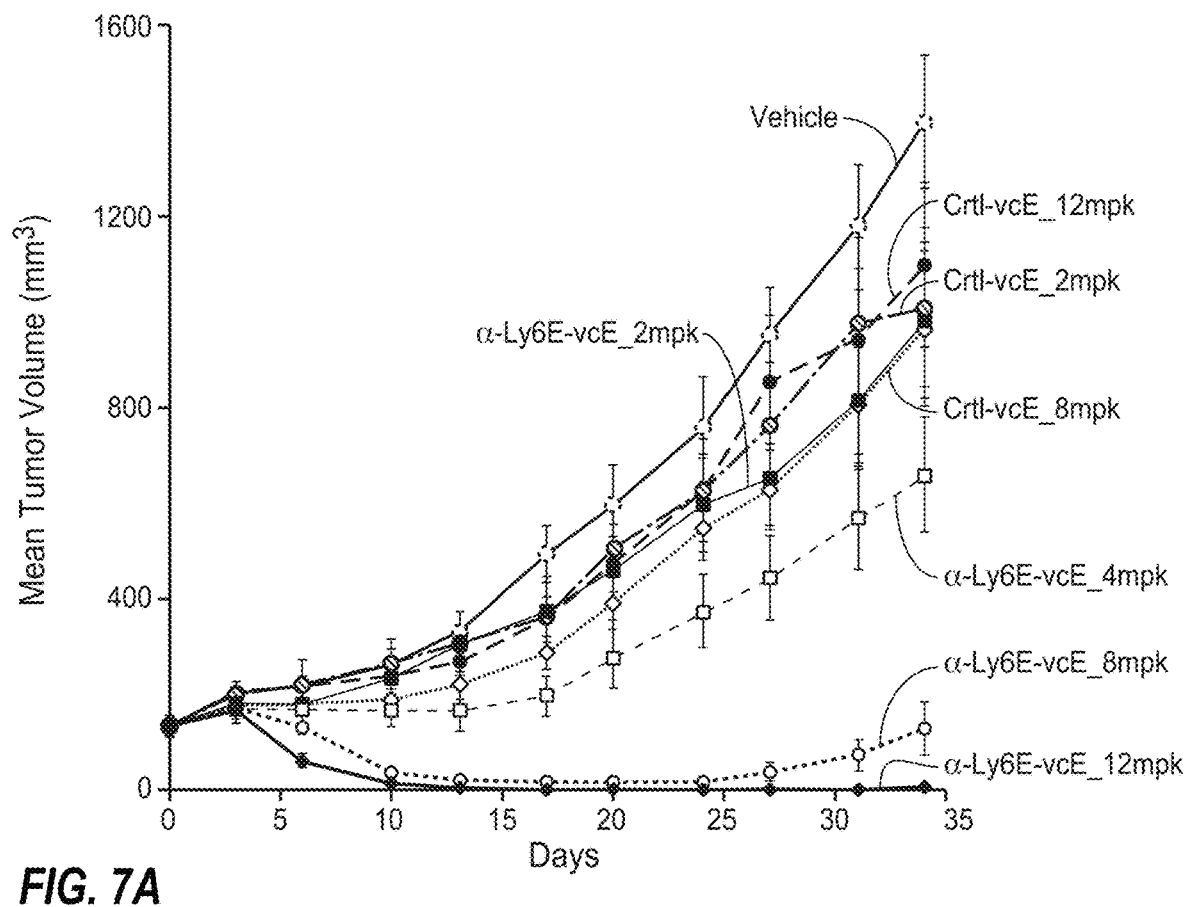
FIGS. 7A-E show the in vivo efficacy of anti-Ly6E ADC, as described in FIG. 5, in primary triple-negative (Her2−/ER−/PR−) breast cancer tumor xenograft model HBCx-9 established at XenTech (Evry, France). Panel A shows subcutaneous tumors established in immunodeficient mice implanted with patient derived breast cancer tumor material. When tumor volumes reached approximately 100-250 mm$^3$ (day 0), animals were given a single IV injection of either control ADC (Control-vc-MMAE) or anti-Ly6E ADC at the indicated doses. Average tumor volumes with standard deviations were determined from 9 animals per groups (indicated on graph). Panel B compares total Ly6E protein expression in various XenTech primary tumor models and in HCC1569 X1 and SU.86.86 cell lysates by immunoblotting with mouse anti-Ly6E antibody 4D8. Total β-Actin protein levels were measured in parallel to serve as loading controls. Panel C shows Ly6E staining on HBCx-9 tumors by immunohistochemistry. Independent staining of multiple tumor samples showed heterogeneous staining patterns. The percent of tumor cells staining at a 1+ level for Ly6E using mouse anti-Ly6E clone 10G7.7.8 is indicated. Panel D shows 2+ Ly6E staining on HBCx-9 tumors by immunohistochemistry using rabbit anti-Ly6E antibody clone GEN-93-8-1. Panel E shows total Ly6E protein expression in HBCx-9 cell lysates by immunoblotting with antibody GEN-93-8-1. GAPDH protein levels were measured in parallel to serve as loading controls.
Figure 7B:
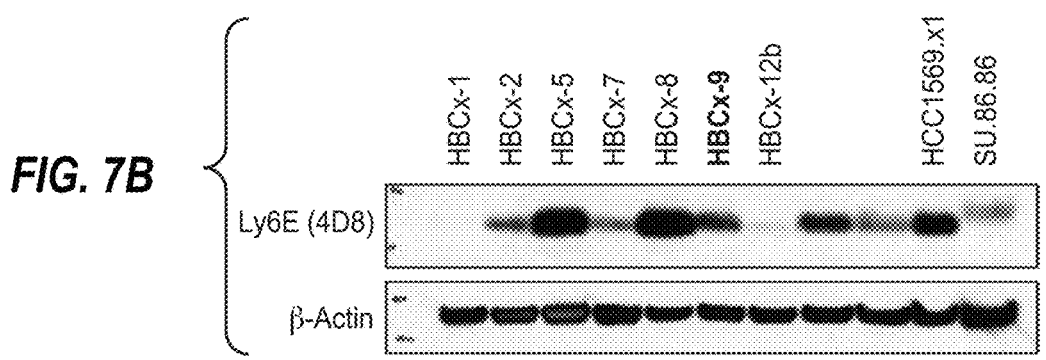
Figure 7C:
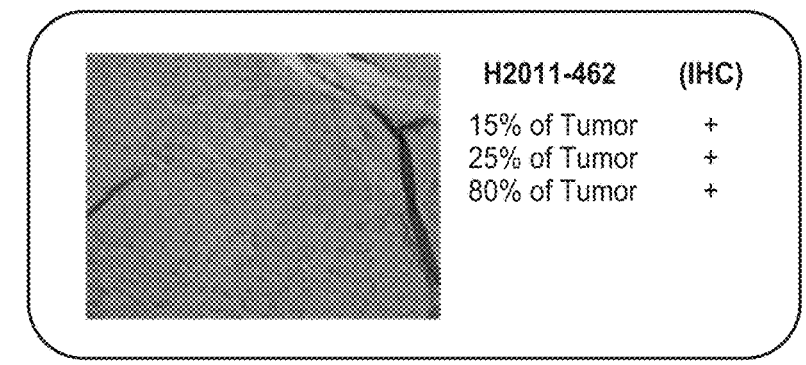
Figure 7D:
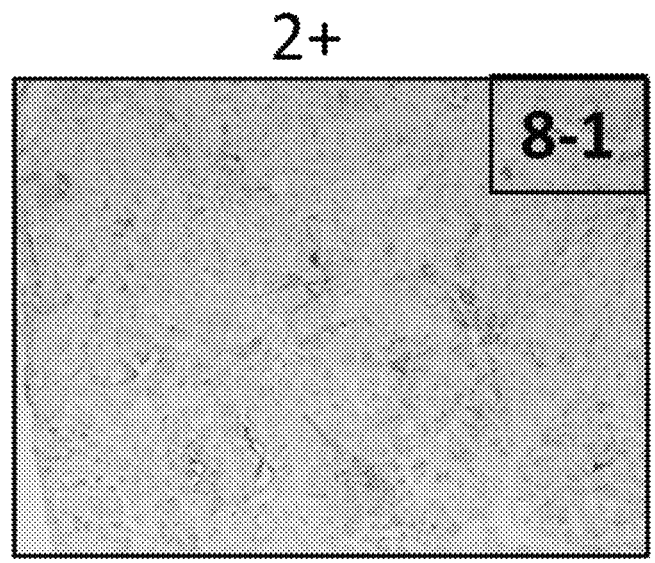
Figure 7E:
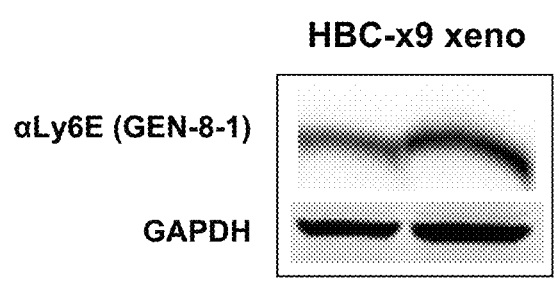
Figure 8D:
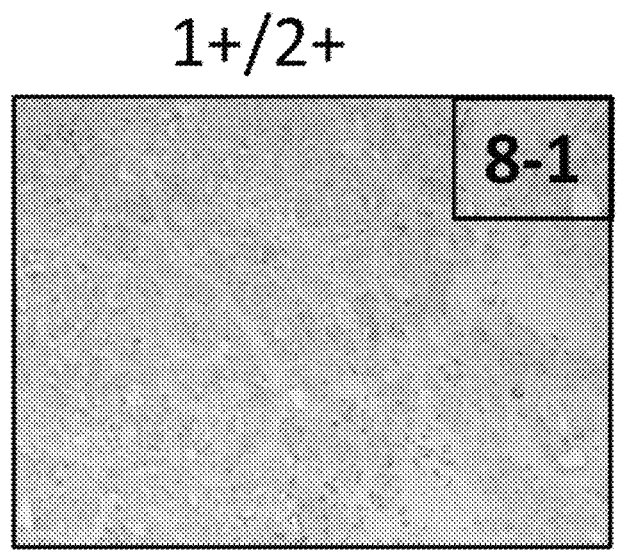
Figure 8E:
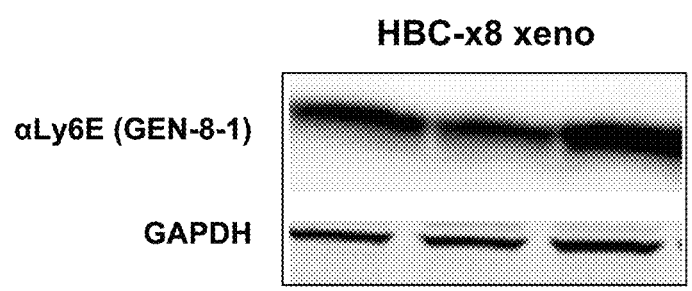
Figure 9A:
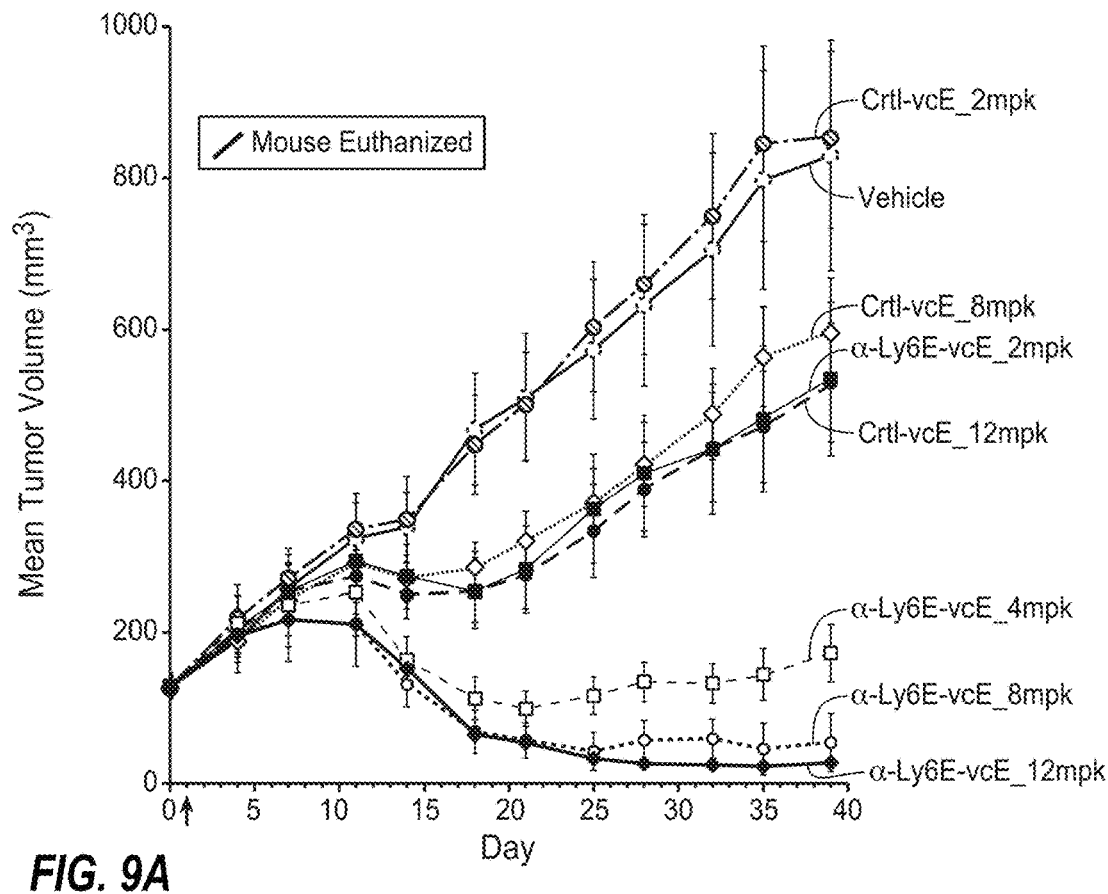
FIGS. 9A-D show the in vivo efficacy of anti-Ly6E ADC, as described in FIG. 5, in primary epidermal growth factor receptor, Her2 amplified breast cancer tumor xenograft model MAXF-1162 established at Oncotest GmbH (Freiburg, Germany). Panel A shows subcutaneous tumors established in immunodeficient mice implanted with patient derived breast cancer tumor material. When tumor volumes reached approximately 100-250 mm$^3$ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various Oncotest primary tumor models and cell lysates by immunoblotting. Total GAPDH protein levels were measured in parallel to serve as loading controls. Panel C shows Ly6E staining on MAXF-1162 tumors by immunohistochemistry using mouse anti-Ly6E clone 10G7.7.8. Independent staining of multiple tumor samples showed heterogeneous staining patterns. The percent of tumor cells staining at a 1+ or 2+ level for Ly6E is indicated. Panel D shows robust 2+ Ly6E staining (and some 1+ staining in the potentially hypoxic central regions) on MAXF-1162 tumors by immunohistochemistry using rabbit anti-Ly6E antibody clone GEN-93-8-1.
Figure 9B:
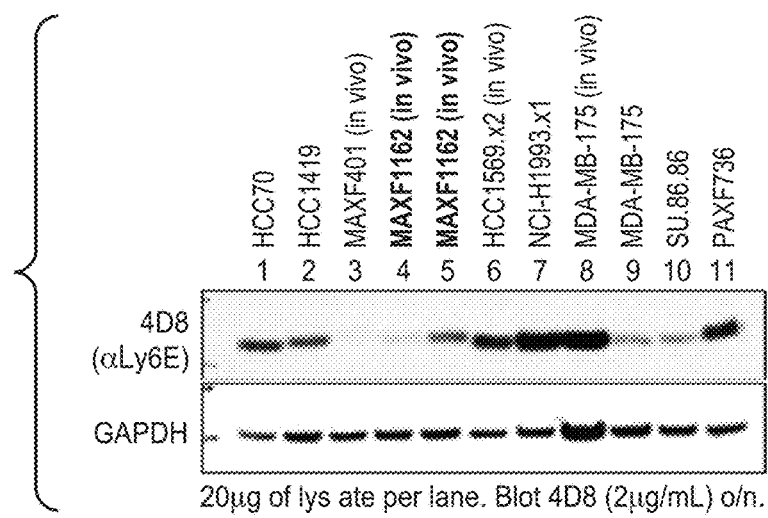
Figure 9C:
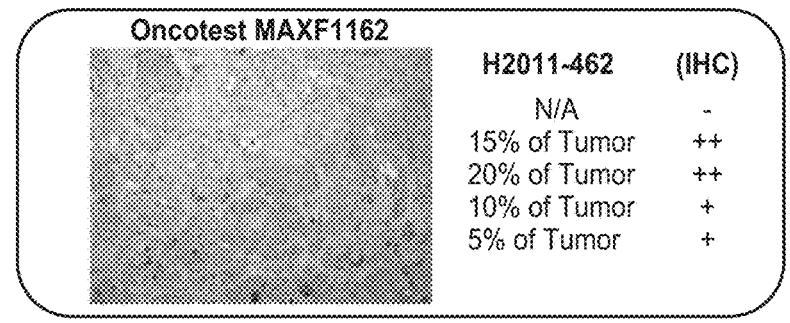
Figure 9D:
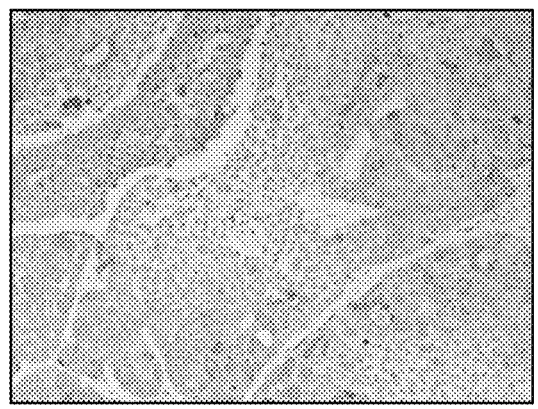
Figure 10A:
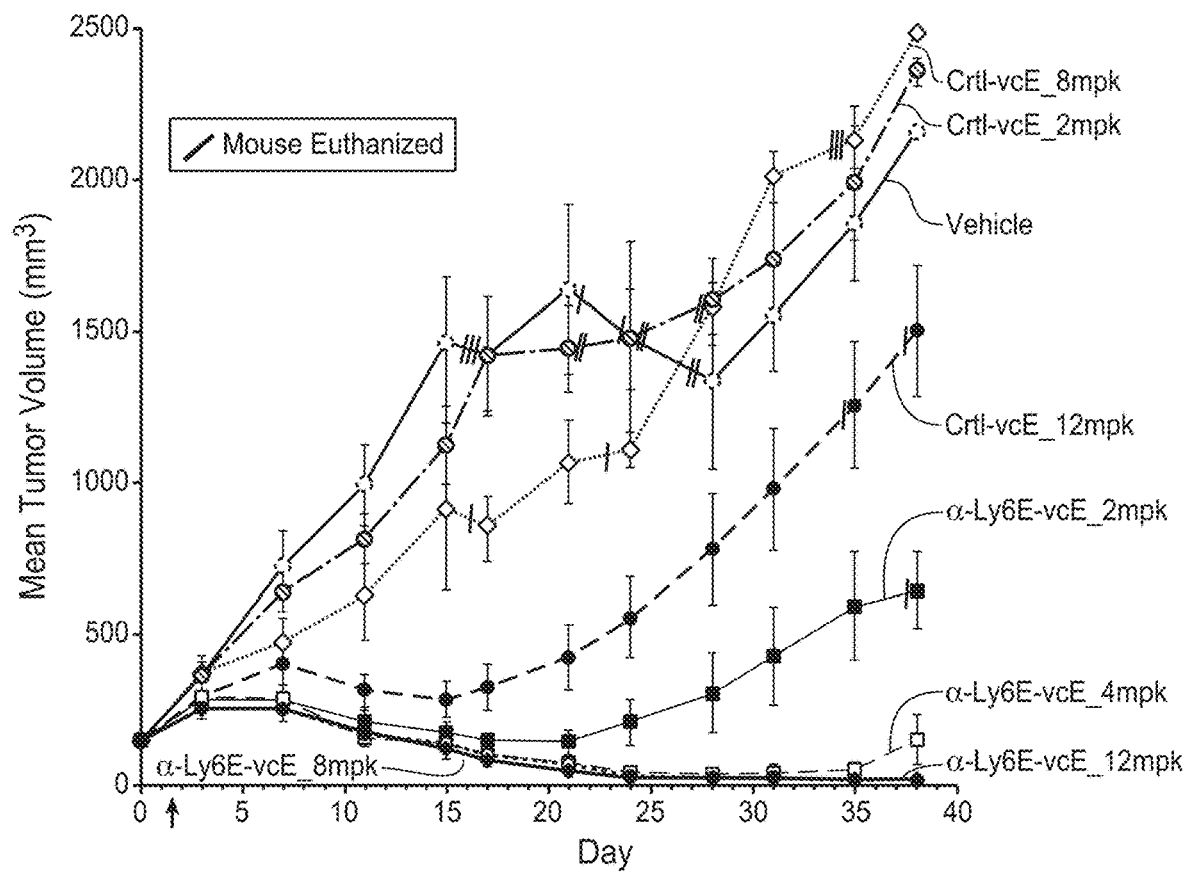
FIGS. 10A-D show the in vivo efficacy of anti-Ly6E ADC, as described in FIG. 5, in primary pancreatic cancer tumor xenograft model PAXF-1657 established at Oncotest GmbH (Freiburg, Germany). Panel A shows subcutaneous tumors established in immunodeficient mice with patient derived pancreatic cancer tumor explants. When tumor volumes reached approximately 100-250 mm$^3$ (day 0), animals were given a single IV injection of either control ADC (Control-vc-MMAE) or anti-Ly6E ADC at the indicated doses. Average tumor volumes with standard deviations were determined from 10 animals per groups (indicated on graph). Panel B compares total Ly6E protein expression in various primary tumor models and cell lysates by immunoblotting. Total GAPDH or β-actin protein levels were measured in parallel to serve as loading controls. Panel C shows Ly6E staining on PAXF-1657 tumors by immunohistochemistry using mouse anti-Ly6E clone 10G7.7.8. Independent staining of multiple tumor samples showed heterogeneous staining patterns. The percent of tumor cells staining at a very weak (+/−) level for Ly6E is indicated. Panel D shows 2+ Ly6E staining on PAXF-1657 tumors by immunohistochemistry using rabbit anti-Ly6E antibody clone GEN-93-8-1.
Figure 10B:
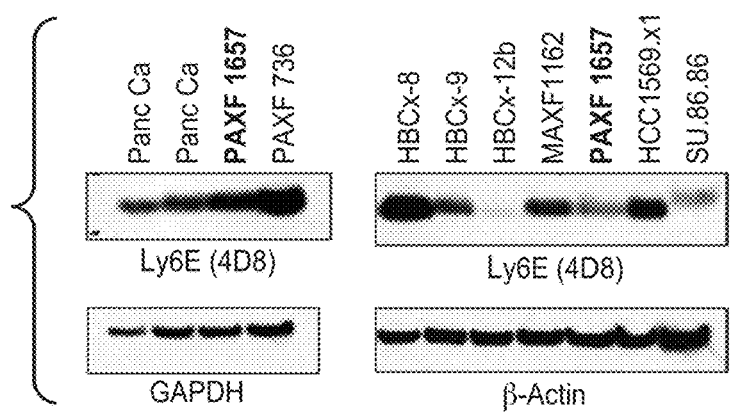
Figure 10C:
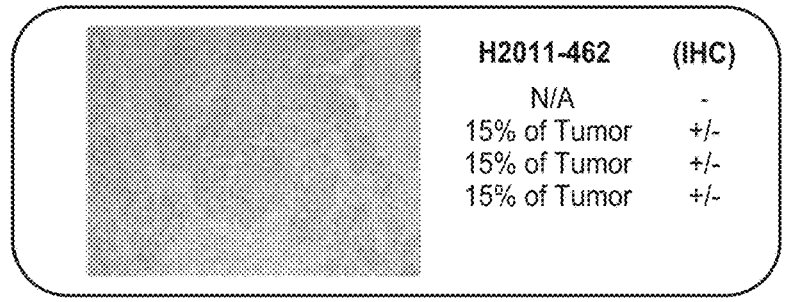
Figure 10D:
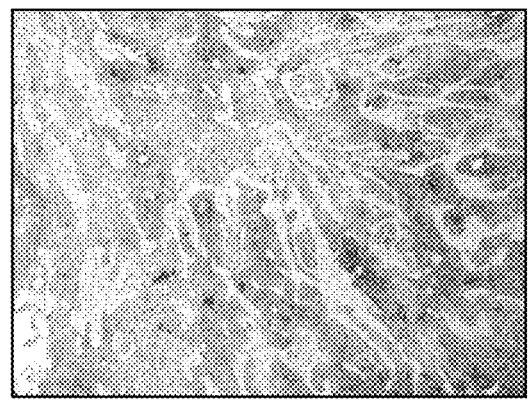

The results indicate that the Ly6E transcript expression in normal tissues is low compared to expression of Ly6E in breast and pancreatic cancers (FIG. 3).

Example 3

Rabbit Monoclonal Antibody Generation

Three rabbits were immunized with bacterial (*Escherichia Coli*) generated His tagged Ly6E (YenZym, South San Francisco, Calif.). Serum titers against Ly6E using test bleeds were evaluated using standard protocols. One rabbit was found to have a good immune response, and was chosen as the candidate for splenectomy and monoclonal fusion.

Four days after a final IV boost of antigen, a splenectomy was performed. Splenocytes were isolated, and $200 \times 10^6$ lymphocyte cells were fused with $100 \times 10^6$ fusion partner cells and plated onto 20 96-well plates (Epitomics, Burlingame, Calif.). The plates were cultured under standard conditions.

Plates were screened using a standard ELISA protocol, with plates coated with 50 ng of human Ly6E per well. Eleven clones were selected and expanded into 24-well plates. Seven of the clones were confirmed positive for anti-Ly6E antibodies. Three of the seven clones were selected to be subcloned using a limited cell dilution method. From the subcloned lines, three hybridomas were selected to be expanded and frozen, including clone GEN-93-8-1.

After further testing, GEN-93-8-1 was selected for molecular cloning and recombinant expression in HEK293 cells. Briefly, mRNA from hybridoma cells was isolated using TURBOCAPTURE® Kit (Qiagen: Catalog #72232) following the manufacturer's instructions and then reverse transcribed into cDNA using oligo-dT primer. The variable region of the heavy chain (VH) was PCR amplified. The entire light chain (LC) was PCR. The PCR-amplified VH region was digested using restriction enzymes HindIII and Kpnl. The PCR-amplified LC was digested using restriction enzymes HindIII and NotI. Digested products were purified using Qiagen QIAQUICK® PCR Purification Kit (catalog #28014). After purification, the VH and LC were ligated into heavy or light chain expression vectors and transformed into DH5α cells (MC Lab, catalog #DA-100). Transformed colonies were picked and inserts were confirmed by expected size (approximately 440 bp for VH and 740 bp for LC) using the corresponding restriction enzymes. Plasmids with inserts of the expected size were sequenced using TT5 primer. The sequences of the heavy chain variable region and the light chain variable region are shown in FIG. 4, and in SEQ ID NOs: 28 and 27, respectively.

Light chain and heavy chain expression vectors were co-transfected into 293 cells in 6-well plates. The supernatants were collected five days post transfection and tested against corresponding antigen. In addition, the IgG concentration was measured. Anti-Ly6E antibody clone GEN-93-8-1 was purified from the cell culture supernatants using Protein A.

Example 4

Ly6E Expression in Malignant and Normal Tissues and in Primary Tumor Models Determined by Immunohistochemistry Immunohistochemistry (IHC) was performed on a Ventana Discovery XT autostainer (Ventana Medical Systems; Tucson, Ariz.). Formalin-fixed, paraffin-embedded whole tissue and tissue microarray sections were deparaffinized and pretreated with CC1 solution (Ventana Medical Systems) for 60 minutes followed by incubation with either 0.2 µg/mL anti-Ly6E antibody clone GEN-93-8-1 or naive rabbit IgG (Clone DAZE, Cell Signaling Technologies; Danvers, Mass.) for 60 minutes at 37° C. Detection was performed with 32-minute OmniMap anti-rabbit horseradish peroxidase (HRP) incubation and diaminobenzidine (DAB) (Ventana Medical Systems) followed by counter staining with hematoxylin II (Ventana Medical Systems).

Staining intensity scores took into account both intensity of staining and proportion of labeled cells. Positive expression was defined as staining in greater than 50% of the tumor cells. Intensity scores are defined in Table 3.

TABLE 3

IHC scoring

| Score | Definition |
|---|---|
| Negative | No detectable signal in >50% of tumor cells |
| 1+ | Positive signal in >50% of tumor cells with majority of signal = weak |
| 2+ | Positive signal in >50% of tumor cells with majority of signal = moderate |
| 3+ | Positive signal in >50% of tumor cells with majority of signal = strong |

The reactivity of the rabbit anti-Ly6E antibody clone GEN-93-8-1 on human tumors was assessed by IHC performed on human breast cancer (N=90, including triple-negative breast tumors (N=39) and Her2−/hormone receptor+(HR+) breast tumors (N=51)), pancreatic adenocarcinoma (N=78), non-small cell lung cancer (N=276, including adenocarcinoma (N=205) and squamous cell carcinoma (N=71)), ovarian carcinoma (N=57), head/neck squamous carcinoma (N=61), gastric adenocarcinoma (N=94), and colorectal adenocarcinoma (N=106) tissue microarrays.

Results of Ly6E IHC are presented in Table 4. In breast cancer samples, 94% of TNBC cases and 81% of Her2−/HR+ cases were positive for Ly6E by IHC staining, with 79% of TNBC cases and 61% of Her2−/HR+ cases showing moderate or strong levels of staining (2+ or 3+ by IHC).

In a set of Her2+ and Her2− breast cancer samples, 87% (130 cases) were positive for Ly6E by IHC staining. Expression was seen in 65%-68% of breast cancers at moderate or strong levels (2+ or 3+). Localization was cytoplasmic/membranous in nature. Weak to moderate Ly6E expression was noted in both normal and normal adjacent-carcinoma breast tissue. In contrast, as noted above, IHC studies using mouse anti-Ly6E clone 10G7.7.8 detected Ly6E in only 27-36% of breast cancers.

Ly6E was highly expressed in pancreatic ductal adenocarcinoma, with 89% of the samples (69 cases) staining positive for Ly6E by IHC, and 63% showing moderate or strong levels of staining (2+ or 3+ by IHC). None of normal pancreas samples (N=5) showed expression of Ly6E. In contrast, as noted above, IHC studies using mouse anti-Ly6E clone 10G7.7.8 detected Ly6E in only ~40% of pancreatic cancers.

Ly6E was expressed in non-small cell lung cancers, with 89% of adenocarcinoma and 83% of squamous cell carcinoma staining positive for Ly6E by IHC, with 64% of adenocarcinoma and 46% of squamous cell carcinoma showing moderate or strong levels of staining (2+ or 3+ by IHC). In contrast, as noted above, IHC studies using mouse anti-Ly6E clone 10G7.7.8 detected Ly6E in only ~29% of non-small cell lung cancers.

The predominant staining in lung cancer was cytoplasmic/membranous. Staining was noted in normal alveolar macrophages at about 1+ (N=12), although it is not clear whether the staining was specific to Ly6E or hemosiderin. No staining was observed on normal pneumocytes.

In colorectal cancer samples, 64% (68 cases) were positive for Ly6E by IHC staining, with 11% of cases showing moderate or strong levels of staining (2+ or 3+ by IHC). In approximately two-thirds of the positive samples, the Ly6E staining was polarized to the apical surface of the carcinoma cells. Normal colon samples tested showed no expression of Ly6E (N=2). In contrast, as noted above, IHC studies using mouse anti-Ly6E clone 10G7.7.8 detected Ly6E in only ~26% of colon cancers.

In ovarian carcinoma, 77% of cases were positive for Ly6E by IHC staining, with 53% of cases showing moderate or strong levels of staining (2+ or 3+ by IHC). In head and neck squamous carcinoma, 85% of cases were positive for Ly6E by IHC staining, with 42% of cases showing moderate or strong levels of staining (2+ or 3+ by IHC). Finally, in gastric adenocarcinoma, 70% of cases were positive for Ly6E by IHC staining, with 31% of cases showing moderate or strong levels of staining (2+ or 3+ by IHC).

Naïve isotype controls were negative on all control samples at 0.2 µg/mL.

TABLE 4

Ly6E IHC in Various Human Cancers

| Cancer type | | Prevalence: IHC (%) | | | | % IHC 1+/ 2+/3+ | % IHC 2+/3+ |
|---|---|---|---|---|---|---|---|
| | N | 0 | 1+ | 2+ | 3+ | | |
| Her2− Breast Cancers | — | 17 | 19 | 40 | 24 | 83 | 64 |
| Sub-   TNBC (15%) | 39 | 5 | 15 | 33 | 46 | 94 | 79 |
| types  Her2−, HR+ (70%) | 51 | 20 | 20 | 41 | 20 | 81 | 61 |
| NSCLC | — | 13 | 30 | 46 | 10 | 86 | 56 |
| Sub-   Adenocarcinoma (40%) | 205 | 11 | 25 | 51 | 13 | 89 | 64 |
| types  Squamous (30%) | 71 | 17 | 37 | 39 | 7 | 83 | 46 |
| Pancreatic Adenocarcinoma | 78 | 12 | 26 | 50 | 13 | 89 | 63 |
| Ovarian Carcinoma | 57 | 23 | 24 | 44 | 9 | 77 | 53 |
| Head/Neck Squamous Carcinoma | 61 | 15 | 43 | 39 | 3 | 85 | 42 |
| Gastric Adenocarcinoma | 94 | 30 | 39 | 27 | 4 | 70 | 31 |
| Colorectal Adenocarcinoma | 106 | 36 | 53 | 10 | 1 | 64 | 11 |

IHC = immunohistochemistry.

Notes:
Staining intensity took into account both intensity of staining and the observation of staining in >50% of the tumor cells: negative = no detectable signal; 1+ = weak signal; 2+ = moderate signal; 3+ = strong signal.

Example 5

Relative Expression of Ly6E in Human and Cynomolgus Monkey Normal Tissues by IHC Staining A normal human tissue microarray (TMA) was stained with the rabbit anti-Ly6E antibody GEN-93-8-1. Weak (1+) positive staining was observed in spleen, breast, adrenal gland, salivary gland, cervix, and endometrium of uterus, and moderate (2+) positive staining was observed in cerebral cortex and cerebellum. Normal cynomolgus monkey tissues stained with the same anti-Ly6E antibody revealed weak (1+) expression in normal breast tissue and moderate (2+) staining in spleen, endometrium of uterus, and urinary bladder epithelium. See Table 5.

TABLE 5

Expression of Ly6E in human and cynomolgus monkey normal tissues by IHC staining

| Normal Tissue | Human | Cyno |
| --- | --- | --- |
| Adrenal gland | WEAK | NO |
| Bone Marrow | NO | NO |
| Brain | MOD | NO |
| Breast | WEAK | WEAK |
| Cervix | WEAK | NO |
| Colon | NO | NO |
| Esophagus | NO | NO |
| Eye | NO | NO |
| Heart | NO | NO |
| Intestine Small | NO | NO |
| Kidney | NO | NO |
| Larynx | NO | NO |
| Liver | NO | NO |
| Lung | NO | NO |
| Pancreas | NO | NO |
| Pituitary | NO | NO |
| Prostate | NO | NO |
| Salivary Gland | WEAK | NO |
| Skeletal Muscle | NO | NO |
| Skin | NO | NO |
| Spleen | WEAK | MOD |
| Stomach | NO | NO |
| Testis | NO | NO |
| Thymus | NO | NO |
| Thyroid | NO | NO |
| Tonsil | NO | NO |
| Urinary Bladder | ND | MOD |
| Uterus (Endometrium) | WEAK | MOD |

Example 6

Generation of Antibody Drug Conjugates

For larger scale antibody production, antibody hu9B12.v12 wa produced in CHO cells. Vectors coding for VL and VH were transfected into CHO cells and IgG was purified from cell culture media by protein A affinity chromatography.

Generation of vcMMAE ADC: Anti-Ly6E antibody-drug conjugates (ADCs) were produced by conjugating hu9B12.v12 or control anti gD ADCs were conjugated to the drug-linker moiety MC-vc-PAB-MMAE, which is depicted herein. For convenience, the drug-linker moiety MC-vc-PAB-MMAE is sometimes referred to in these Examples and in the Figures as "vcMMAE" or "VCE." Prior to conjugation, the antibodies were partially reduced with TCEP using standard methods in accordance with the methodology described in WO 2004/010957 A2. The partially reduced antibodies were conjugated to the drug-linker moiety using standard methods in accordance with the methodology described, e.g., in Doronina et al. (2003) Nat. Biotechnol. 21:778-784 and US 2005/0238649 A1. Briefly, the partially reduced antibodies were combined with the drug-linker moiety to allow conjugation of the drug-linker moiety to reduced cysteine residues of the antibody. The conjugation reactions were quenched, and the ADCs were purified. The drug load (average number of drug moieties per antibody) for each ADC was determined and was between 3.3 and 4.0 for the anti-Ly6E antibodies and anti-gD control antibodies.

Example 7

In Vivo Efficacy of Anti-Ly6E ADC in Xenograft Mouse Models and IHC Staining of Cancer Cell Lines Breast cancer cell line, HCC1569 (CRL-2330) and pancreatic cancer cell line SU.86.86 (CRL-1837) were obtained from American Type Culture Collection (ATCC, Manassas, Va.). CHO-K1S is a suspension cell line derivative of CHO-K1. The HCC1569 X2 cell line is a derivative of the parental HCC1569 cell line (ATCC, CRL-2330) optimized for growth in vivo. Parental HCC1569 cells were injected subcutaneously in the right flank of female Taconic NCr nude mice, one tumor was harvested, minced and grown in vitro resulting in the HCC1569 X1 cell line. The HCC1569 X1 line was injected again subcutaneously in the right flank of female Taconic NCr nude mice in an effort to improve the growth of the cell line. A tumor from this study was collected and again adapted for in vitro growth to generate the HCC1569 X2 cell line. This cell line and tumors derived from this line express Ly6E.

Xenograft models: Efficacy of anti-Ly6E antibody drug conjugates (ADCs) was evaluated in xenograft models derived from cell lines described above or in primary patient derived tumor models, the latter experiments were conducted at Oncotest, Freiburg, Germany and in XenTech, Genopole, France.

All studies conducted at Genentech, South San Francisco, Calif. were in accordance with the Guide for the Care and Use of Laboratory Animals (Ref: Institute of Laboratory Animal Resources (NIH publication no. 85-23), Washington, D.C.: National Academies Press; 1996). All experiments conducted at Oncotest were approved by the local authorities, and are conducted according to the guidelines of the German Animal Welfare Act (Tierschutzgesetz). The authorization to use animals in the CERFE facilities of XenTech was obtained by The Direction des Services Veterinaires, Ministere de l'Agriculture et de la Pêche, France (agreement No. A 91-228-107). The animal care and housing are in accordance with European Convention STE 123. All experiments at XenTech will be performed in accordance with French legislation concerning the protection of laboratory animals and in accordance with a currently valid license for experiments on vertebrate animals, issued by the French Ministry for Agriculture and Fisheries to Dr. Truong-An TRAN (No. A 91-541 dated 21 Dec. 2010; validity: 5 years). 6- to 9-week old female immunodeficient mice were inoculated subcutaneously in the dorsal right flank and average tumor volumes with SDs were determined from 9-10 mice per group.

For efficacy studies with xenografts derived from cell lines, NCR nude mice from Taconic were inoculated with 5 million cells in HBSS with Matrigel or C.B-17 SCID (inbred) mice From Charles River were inoculated with 2 million cells in HBSS with Matrigel. 0.36 mg estrogen implants were used for the HCC1569 X2 xenograft model. For efficacy studies with tumor explants at XenTech and Oncotest, athymic nude or NMRI nu/nu mice from Harlan or Charles River were implanted with primary breast or pancreatic cancer patient derived materials from models HBCx-8, HBCx-9, MAXF-1162 and PAXF-1657. When tumor volumes reached approximately 80-200 mm3 (day 0), animals were randomized into groups of 9-10 each and administered a single intravenous (IV) injection of either vehicle control or the ADC at the appropriate dose. Tumor volumes were measured twice per week until study end.

As shown in FIGS. 5 to 10, rabbit anti-Ly6E antibody clone GEN-93-8-1 is more sensitive than the previous immunohistochemistry antibody, mouse ant-Ly6E antibody clone 10G7.7.8.

In an HCC1569 X2 breast cancer xenograft model, immunohistochemistry with GEN-93-8-1 showed 3+ staining, while 10G7.7.8 showed lower 1+/2+ staining. See FIG. 5, panels E an D, respectively. HCC1569 X2 breast cancer cells are Her2/neu+ and ER–/PR–/p53–. The HCC1569 X2 breast cancer xenograft model was sensitive to humanized anti-Ly6E (hu9B12 v12) ADC (MC-vc-PAB-MMAE) at 2 mg/kg and 4 mg/kg. See FIG. 5, panel A.

In an SU.86.86 pancreatic cancer xenograft model, immunohistochemistry with GEN-93-8-1 showed 2+ staining, while 10G7.7.8 showed lower 1+/2+ staining. See FIG. 6, panels E and C, respectively. The SU.86.86 pancreatic cancer xenograft model was sensitive to humanized anti-Ly6E (hu9B12 v12) ADC (MC-vc-PAB-MMAE) at 1 mg/kg and 3 mg/kg. See FIG. 6, panel A.

In an HBCx-9 breast cancer xenograft model, immunohistochemistry with GEN-93-8-1 showed 2+ staining, while 10G7.7.8 showed lower 1+ staining. See FIG. 7, panels D and C, respectively. HBCx-9 breast cancer cells are triple negative (Her2–/ER–/PR–). The HBCx-9 breast cancer xenograft model was sensitive to humanized anti-Ly6E (hu9B12 v12) ADC (MC-vc-PAB-MMAE) at 8 mg/kg and 12 mg/kg. See FIG. 7, panel A.

In an HBCx-8 breast cancer xenograft model, immunohistochemistry with GEN-93-8-1 and 10G7.7.8 showed 1+/2+ staining; however the staining with GEN-93-8-1 was more robust and homogenous compared to staining with 10G7.7.8. See FIG. 8, panels D and C, respectively. HBCx-8 breast cancer cells are triple negative (Her2–/ER–/PR–). The HBCx-8 breast cancer xenograft model was sensitive to humanized anti-Ly6E (hu9B12 v12) ADC (MC-vc-PAB-MMAE) at 12 mg/kg. See FIG. 8, panel A.

In a MAXF-1162 breast cancer xenograft model, immunohistochemistry with GEN-93-8-1 showed robust 2+ staining (with some 1+ staining in the central hypoxic region), while 10G7.7.8 showed less homogenous 1+/2+ staining. See FIG. 9, panels D and C, respectively. MAXF-1162 breast cancer cells have Her2 amplification. The MAXF-1162 breast cancer xenograft model was sensitive to humanized anti-Ly6E (hu9B12 v12) ADC (MC-vc-PAB-MMAE) at 4 mg/kg, 8 mg/kg, and 12 mg/kg. See FIG. 9, panel A.

In a PAXF-1657 pancreatic cancer xenograft model, immunohistochemistry with GEN-93-8-1 showed robust 2+ staining, while 10G7.7.8 showed weak +/– staining. See FIG. 10, panels D and C, respectively. The PAXF-1657 pancreatic cancer xenograft model was sensitive to humanized anti-Ly6E (hu9B12 v12) ADC (MC-vc-PAB-MMAE) at 2 mg/kg, 4 mg/kg, 8 mg/kg, and 12 mg/kg. See FIG. 10, panel A.

Overall, GEN-93-8-1 showed more robust and homogenous staining by IHC as compared to 10G7.7.8.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An in vitro method of detecting human Ly6E in a biological sample comprising contacting the biological sample with an isolated antibody that binds to human Ly6E comprising the amino acid sequence of SEQ ID NO: 38, wherein the antibody comprises (a) HVR-H1 comprising the amino acid sequence of SEQ ID NO:32, (b) HVR-H2 comprising the amino acid sequence of SEQ ID NO:33, (c) HVR-H3 comprising the amino acid sequence of SEQ ID NO:34, (d) HVR-L1 comprising the amino acid sequence of SEQ ID NO:29, (e) HVR-L2 comprising the amino acid sequence of SEQ ID NO:30, and (f) HVR-L3 comprising the amino acid sequence of SEQ ID NO:31, and detecting whether a complex is formed between the anti-Ly6E antibody and the human Ly6E in the biological sample, wherein the method comprises a control, and
   wherein (i) the antibody is conjugated to a label and detecting the complex comprises detecting the label; or
   (ii) detecting the complex comprises detecting the antibody with a labeled secondary antibody.

2. The method of claim 1, wherein the anti-Ly6E antibody comprises (a) a VH sequence of SEQ ID NO:28; (b) a VL sequence of SEQ ID NO: 27; or (c) a VH sequence of SEQ ID NO:28 and a VL sequence of SEQ ID NO:27.

3. The method of claim 1, wherein the biological sample is a breast cancer sample, a pancreatic cancer sample, a colon cancer sample, a colorectal cancer sample, a melanoma cancer sample, an ovarian cancer sample, a non-small cell lung cancer sample, an esophageal cancer sample, a head and neck cancer sample, a kidney cancer sample, a soft tissue cancer sample, an endometrial cancer sample, or a gastric cancer sample.

4. The method of claim 1, wherein the anti-Ly6E antibody comprises (a) a VH sequence having at least 95% sequence identity to the amino acid sequence of SEQ ID NO:28; (b) a VL sequence having at least 95% sequence identity to the amino acid sequence of SEQ ID NO: 27; or (c) a VH sequence as in (a) and a VL sequence as in (b).

5. The method of claim 1, wherein the anti-Ly6E antibody is a monoclonal antibody.

6. The method of claim 5, wherein the anti-Ly6E antibody is a rabbit, humanized, or chimeric antibody.

7. The method of claim 5, wherein the anti-Ly6E antibody is an IgG selected from IgG1, IgG2a, IgG2b, IgG3, and IgG4.

8. The method of claim 1, wherein the anti-Ly6E antibody is conjugated to a label.

9. The method of claim 1, wherein the biological sample is a breast cancer sample from a Her2 positive breast cancer, a Her2 negative breast cancer, a Her2 negative/hormone receptor positive (Her2−/ER+/PR+) breast cancer, or a triple negative (Her2−/ER−/PR−) breast cancer.

10. The method of claim 1, wherein the biological sample is a gastric cancer sample from a Her2 positive gastric cancer or a Her2 negative gastric cancer.

11. The method of claim 8, wherein the label is a positron emitter, a radioisotope, a fluorophore, a luciferase, a horseradish peroxidase, an alkaline phosphatase, a P-galactosidase, a glucoamylase, a lysozyme, a saccharide oxidase, biotin, avidin, a ligand, a spin label, a bacteriophage label, or a stable free radical.

12. An in vitro method of detecting human Ly6E in a biological sample comprising contacting the biological sample with an isolated antibody that binds to human Ly6E comprising the amino acid sequence of SEQ ID NO: 38, wherein the antibody comprises a VH sequence of SEQ ID NO:28 and a VL sequence of SEQ ID NO:27, and detecting whether a complex is formed between the anti-Ly6E antibody and the human Ly6E in the biological sample, wherein the method comprises a control, and
   wherein (i) the antibody is conjugated to a label and detecting the complex comprises detecting the label; or (ii) detecting the complex comprises detecting the antibody with a labeled secondary antibody.

13. The method of claim 12, wherein the biological sample is a breast cancer sample, a pancreatic cancer sample, a colon cancer sample, a colorectal cancer sample, a melanoma cancer sample, an ovarian cancer sample, a non-small cell lung cancer sample, an esophageal cancer sample, a head and neck cancer sample, a kidney cancer sample, a soft tissue cancer sample, an endometrial cancer sample, or a gastric cancer sample.

14. The method of claim 12, wherein the anti-Ly6E antibody is a monoclonal antibody.

15. The method of claim 14, wherein the anti-Ly6E antibody is a rabbit or chimeric antibody.

16. The method of claim 14, wherein the anti-Ly6E antibody is an IgG selected from IgG1, IgG2a, IgG2b, IgG3, and IgG4.

17. The method of claim 12, wherein the anti-Ly6E antibody is conjugated to a label.

18. The method of claim 12, wherein the biological sample is a breast cancer sample from a Her2 positive breast cancer, a Her2 negative breast cancer, a Her2 negative/hormone receptor positive (Her2−/ER+/PR+) breast cancer, or a triple negative (Her2−/ER−/PR−) breast cancer.

19. The method of claim 12, wherein the biological sample is a gastric cancer sample from a Her2 positive gastric cancer or a Her2 negative gastric cancer.

20. The method of claim 17, wherein the label is a positron emitter, a radioisotope, a fluorophore, a luciferase, a horseradish peroxidase, an alkaline phosphatase, a P-galactosidase, a glucoamylase, a lysozyme, a saccharide oxidase, biotin, avidin, a ligand, a spin label, a bacteriophage label, or a stable free radical.

* * * * *

UNITED STATES PATENT AND TRADEMARK OFFICE
CERTIFICATE OF CORRECTION

PATENT NO. : 10,889,651 B2
APPLICATION NO. : 16/050936
DATED : January 12, 2021
INVENTOR(S) : Jyoti Asundi et al.

Page 1 of 1

It is certified that error appears in the above-identified patent and that said Letters Patent is hereby corrected as shown below:

In the Claims

In Claim 11, Column 78, Lines 58-59, "P-galactosidase" should read --β galactosidase--

In Claim 20, Column 80, Lines 16-17, "P-galactosidase" should read --β galactosidase--

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*